(12) United States Patent
Sugita et al.

(10) Patent No.: US 7,847,063 B2
(45) Date of Patent: Dec. 7, 2010

(54) GLP-1 DERIVATIVE

(75) Inventors: Koichi Sugita, Tokyo (JP); Saori Kasahara, Tokyo (JP); Hiroyasu Ebinuma, Tokyo (JP); Fumio Takaiwa, Tsukuba (JP); Takahito Jomori, Nagoya (JP); Yuji Hayashi, Nagoya (JP); Akira Tashita, Nagoya (JP); Yukari Kobara, Nagoya (JP)

(73) Assignee: Sanwa Kagaku Kenkyusho Co., Ltd., Aichi (JP)

( * ) Notice: Subject to any disclaimer, the term of this patent is extended or adjusted under 35 U.S.C. 154(b) by 605 days.

(21) Appl. No.: 10/550,624

(22) PCT Filed: Mar. 26, 2004

(86) PCT No.: PCT/JP2004/004382

§ 371 (c)(1),
(2), (4) Date: Jul. 17, 2006

(87) PCT Pub. No.: WO2004/087910

PCT Pub. Date: Oct. 14, 2004

(65) Prior Publication Data

US 2007/0033676 A1 Feb. 8, 2007

(30) Foreign Application Priority Data

Mar. 28, 2003 (JP) ............................. 2003-092827

(51) Int. Cl.
*A61K 38/00* (2006.01)
*C07K 14/00* (2006.01)

(52) U.S. Cl. .......................................... 530/324; 514/2

(58) Field of Classification Search ........................ None
See application file for complete search history.

(56) References Cited

U.S. PATENT DOCUMENTS

| 5,545,618 | A | 8/1996 | Buckley et al. | |
| 6,440,930 | B1 * | 8/2002 | Rinella, Jr. | 514/2 |
| 6,903,186 | B1 * | 6/2005 | Dong | 530/324 |
| 7,268,213 | B2 * | 9/2007 | Dong | 530/329 |
| 7,291,594 | B2 * | 11/2007 | Hayashi et al. | 514/12 |
| 7,368,427 | B1 * | 5/2008 | Dong et al. | 514/12 |

FOREIGN PATENT DOCUMENTS

| JP | 2002-299283 | * | 10/2002 |
| JP | 2003-192698 | | 7/2003 |
| WO | WO 00/63401 A1 | | 10/2000 |
| WO | WO 01/55213 A2 | | 8/2001 |
| WO | WO 01/72959 A2 | | 10/2001 |

OTHER PUBLICATIONS

Monroe et al. *Homo sapiens* glucagon (2002) GenBank Accession NM_002054, pp. 1-4.*

WO/2004/037859 Bibliographic data on file with the International Bureau, WIPO, downloaded Jun. 16, 2009.*

English translation of JP 2002-299283 (Priority date=Oct. 11, 2002).*

H. Hosoyama et al., "Introduction of a chimeric gene encoding an oryzacystatin-β-glucuronidase fusion protein into rice protoplasts and regeneration of transformed plants," Plant Cell Reports, vol. 15, No. 3-4, Dec. 1995, pp. 174-177.

M. Terashima et al., "Growth characteristics of rice cell genetically modified for recombinant human $α_1$-antitrypsin production," Biochemical Engineering Journal, vol. 12, No. 2, Nov. 2002, pp. 155-160.

P. Vain, "Expression of an engineered cysteine proteinase inhibitor (Oryzacystatin-1δD8) for nematode resistance in transgenic rice plants," Theoretical and Applied Genetics, vol. 96, No. 2, Feb. 1998, pp. 266-271.

C. Giri et al., "Production of transgenic rice with agronomically useful genes: an assessment," Biotechnology Advances, vol. 18, No. 8, Dec. 1, 2000, pp. 653-683.

P. Roeckel et al., "Effects of seed-specific expression of a cytokinin biosynthetic gene on canola and tobacco phenotypes," Transgenic Research, vol. 6, No. 2, Mar. 1997, pp. 133-141.

D. Yang et al., "Expression and localization of human lysozyme in the endosperm of transgenic rice," Planta, vol. 216, No. 4, Feb. 2003, pp. 597-603.

H. Yasuda et al., "Expression of the small peptide GLP-1 in transgenic plants," Transgenic Research, vol. 14, No. 5, Oct. 2005, pp. 677-684.

Ebinuma, Hiroyasu et al., "Selection of marker-free transgenic plants using the isopentenyl transferase gene", Proc. Natl. Acad. Sci., Mar. 1997, vol. 94, No. 6, pp. 2117-2121.

Horvath, Henriette et al., "The production of recombinant proteins in transgenic barley grains", Proc. Natl. Acad. Sci., Feb. 2000, vol. 97, No. 4, pp. 1914-1919.

Patel, Minesh et al., "Transgenic barley expressing a fungal xylanase gene in the endosperm of the developing grains", Molecular Breeding, 2000, vol. 6, pp. 113-123.

Sojikul, Punchapat et al., "A plant signal peptide-hepatitis B surface antigen fusion protein with enhanced stability and immunogencity expressed in plant cells", Mar. 2003, vol. 100, No. 5, pp. 2209-2214.

(Continued)

*Primary Examiner*—Anand U Desai
(74) *Attorney, Agent, or Firm*—Foley & Lardner LLP

(57) ABSTRACT

The present invention provides a method for highly producing a recombinant protein in a plant storage organ and a GLP-1 derivative. The plant storage organ in which the recombinant protein is highly produced is obtained by transformation with the use of a vector which comprises a recombinant protein gene, a cytokinin-related gene, a drug-resistant gene and a removable DNA element, in which the cytokinin-related gene and the drug-resistant gene exist in the positions so that they can behave together with the DNA element, while the recombinant protein to be expressed in the plant storage organ exists in the position so that it would not behave together with the DNA element. The GLP-1 is produced by using the method, and a derivative having been stabilized against enzymatic digestion is further provided.

4 Claims, 11 Drawing Sheets

OTHER PUBLICATIONS

Sugita, Koichi et al., "Keitai Henka de Marker Free Kumikae Shokubutsu o Senbatsu", Bioscience & Industry, 1997, vol. 55, No. 3, pp. 210-212.

Xue, G. P. et al., "Selectable marker-free transgenic barley producing a high level of cellulose (1,4-β-glucanase) in developing grains", Plant Cell Rep, Jul. 2003, vol. 21, No. 11, pp. 1088-1094.

Yang, Daichang et al., "Expression of the REB transcriptional activator in rice grains improves the yield of recombinant proteins whose genes are controlled by a Reb-responsive promoter", Proc. Natl. Acad, Sci., Sep. 2001, vol. 98, No. 20, pp. 11438-11443.

International Search Report for Intl Appl. No. PCT/JP2004/004382 (2 pages).

* cited by examiner

[Fig. 5]

Lanes 1-7: Strains prepared in Example 1
Lane 8    NIHONBARE (Non-Transformant)
Lane 9    A strain prepared in Example 1 pGlbGLP-Hm

[Fig. 8]
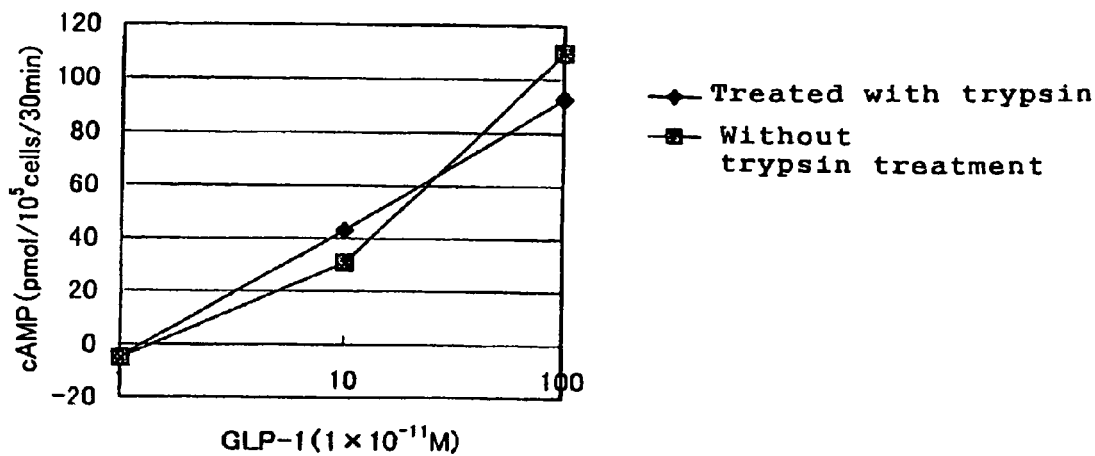
[Fig. 9]
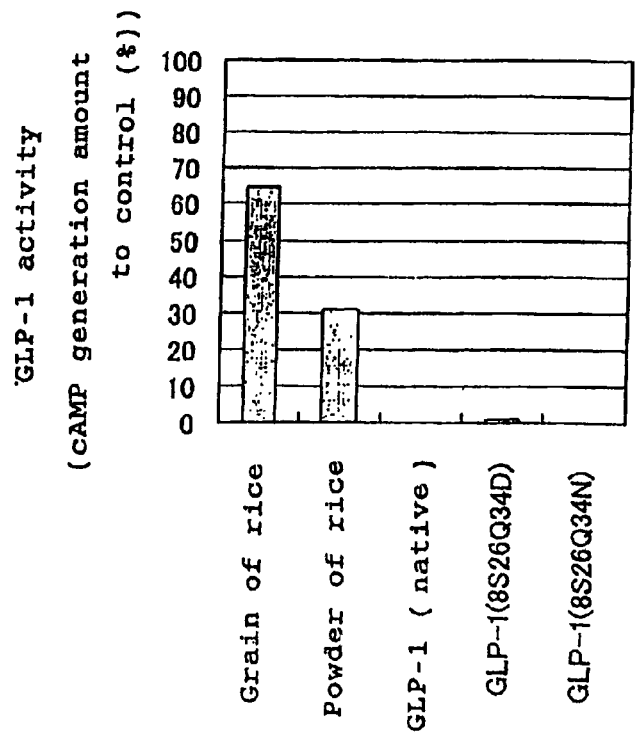

[Fig. 12]
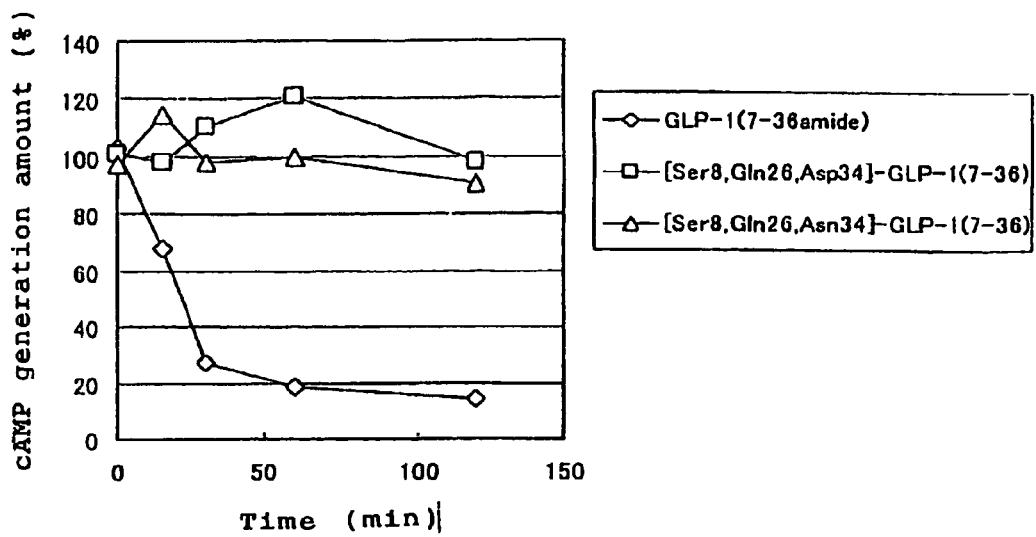
[Fig. 13]
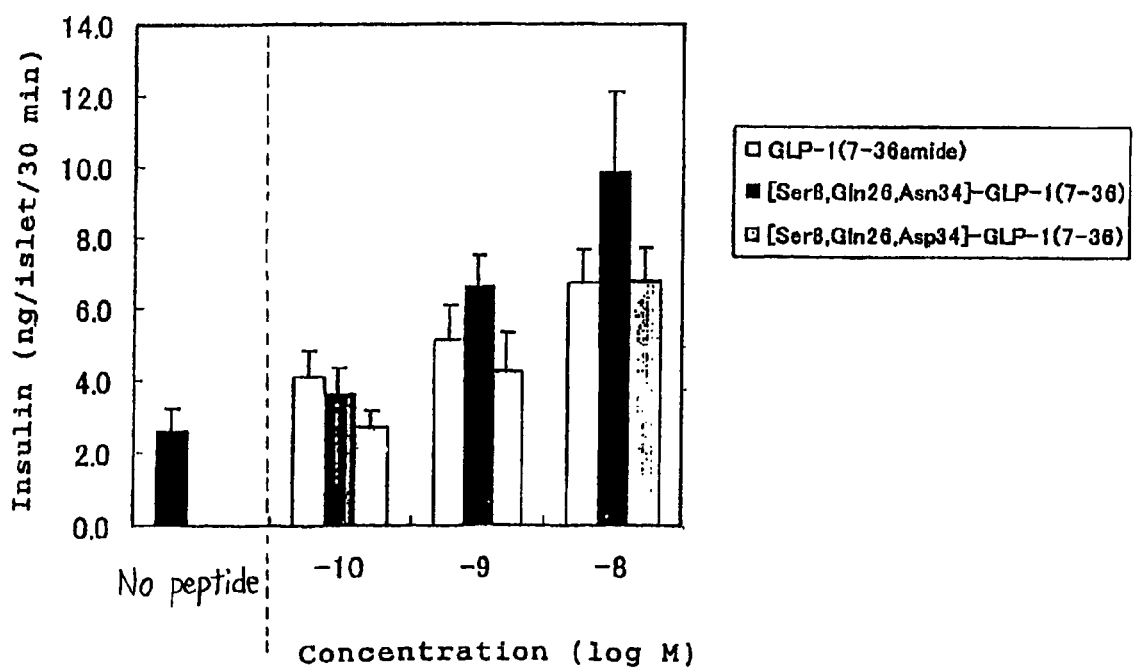

native : GLP-1(7-36amide)

34N : [Ser8,Gln26,Asn34]-GLP-1(7-36)

34D : [Ser8,Gln26,Asp34]-GLP-1(7-36)

5 : 5μg/kg Subcutaneous administration

20 : 20μg/kg Subcutaneous administration

SEQUENCE LISTING

```
<160> NUMBER OF SEQ ID NOS: 7

<210> SEQ ID NO 1
<211> LENGTH: 90
<212> TYPE: DNA
<213> ORGANISM: Artificial Sequence
<220> FEATURE:
<221> NAME/KEY: CDS
<222> LOCATION: (1)..(90)
<220> FEATURE:
<223> OTHER INFORMATION: Description of Artificial Sequence: Synthetic
      nucleotide sequence

<400> SEQUENCE: 1 cat tct gag gga aca ttc aca tct gat gta agt tct tac ctc gag ggc        48
His Ser Glu Gly Thr Phe Thr Ser Asp Val Ser Ser Tyr Leu Glu Gly
  1               5                  10                  15 caa gca gct caa gaa ttc atc gct tgg ctc gta gat ggc cgt              90
Gln Ala Ala Gln Glu Phe Ile Ala Trp Leu Val Asp Gly Arg
             20                  25                  30

<210> SEQ ID NO 2
<211> LENGTH: 30
<212> TYPE: PRT
<213> ORGANISM: Artificial Sequence
<220> FEATURE:
```

```
<223> OTHER INFORMATION: Description of Artificial Sequence: Synthetic
      recombinant protein

<400> SEQUENCE: 2

His Ser Glu Gly Thr Phe Thr Ser Asp Val Ser Ser Tyr Leu Glu Gly
 1               5                  10                  15

Gln Ala Ala Gln Glu Phe Ile Ala Trp Leu Val Asp Gly Arg
            20                  25                  30

<210> SEQ ID NO 3
<211> LENGTH: 24
<212> TYPE: DNA
<213> ORGANISM: Homo sapiens

<400> SEQUENCE: 3
ggatccatgg ctagcaaggt cgtc                                          24

<210> SEQ ID NO 4
<211> LENGTH: 26
<212> TYPE: DNA
<213> ORGANISM: Homo sapiens

<400> SEQUENCE: 4
gatcactatc tcgttgcatg caacac                                        26

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Synthetic
      recombinant protein

<400> SEQUENCE: 5

His Ala Glu Gly Thr Phe Thr Ser Asp Val Ser Ser Tyr Leu Glu Gly
 1               5                  10                  15

Gln Ala Ala Gln Glu Phe Ile Ala Trp Leu Val Asn Gly Arg
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Description of Artificial Sequence: Synthetic
      recombinant protein

<400> SEQUENCE: 6

His Ser Glu Gly Thr Phe Thr Ser Asp Val Ser Ser Tyr Leu Glu Gly
 1               5                  10                  15

Gln Ala Ala Gln Glu Phe Ile Ala Trp Leu Val Asn Gly Arg
            20                  25                  30

<210> SEQ ID NO 7
<211> LENGTH: 30
<212> TYPE: PRT
<213> ORGANISM: Unknown Organism
<220> FEATURE:
<223> OTHER INFORMATION: Description of Unknown Organism: Unknown GLP-1
      protein
```

```
<400> SEQUENCE: 7

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30
```

GLP-1 DERIVATIVE

TECHNICAL FIELD

The present invention relates to a method for producing a plant storage organ in which a recombinant protein is highly produced and a novel derivative of human glucagon-like peptide-1 (GLP-1) which is peptidase-resistant and the use thereof. Meanwhile, the "recombinant protein" in the present invention encompasses "a recombinant peptide and a recombinant protein" (hereinafter referred to as "a recombinant protein").

BACKGROUND ART

Production of pharmaceuticals, clinical diagnostics and industrial materials using genetic engineering technique has greatly contributed to the actual industrial world already, among which substance production systems are particularly widely utilized where cultured cells of microorganisms or mammals are used as host cells. However, culture of these cells requires culture facilities or culture media in completed sterile environment. Further inevitable consumption of petroleum energy causes high cost. In addition, mammal cells cannot be used as hosts without involving the risk of contamination of virus which is harmful to human body.

Consequently, substance production systems using transformed plants have been developed as substance production systems with safety at low cost in stead of substance production systems by culture of cells of microorganisms or mammals. For instance, generation of transformed plants producing: a polymeric compound such as biodegradable polyester (e.g. Japanese Laid-Open Patent Application No.2002-262886), a protein such as a vaccine (e.g. G. Jaeger et al., Eur. J. Biochem. 259, 426, 1999) and lactoferrin (D. Chong et al., Transgenic. Res. 9, 71, 2000), and a peptide such as enkephalin (Japanese-Laid Open Patent Application No. 2000-106890), has been reported so far.

With regard to transformed plants, production of a functional substance being beneficial to human body in edible parts of the plants e.g. seeds of *Glycine max* or *Oryza sativa*, or vegetable leaves, allows the intended substance to be taken orally into human body directly without an extraction process for them. Further, for seeds, refrigeration or transported in facility with refrigerating device is not required, while it can be steadily stored for long time at room temperature. In addition, even when the intended substance is extracted, it can be easily purified, because, unlike leaves, the contamination of phenolic substances seldom occurs with seeds. Accordingly, a seed has been regarded as an ideal organ to produce the intended genetic product, and generation of seeds which produced: proteins such as glycinin (T. Katsube et al., Plant. Physiol. 120, 1063, 1999), enzymes such as (1,3-1,4)-β-glucanase (H. Horvathetal., Proc. Nathl. Acad. Sci. USA., 97,1914, 2000), and peptides such as enkephalin (D. Chong et al., Transgenic. Res., 9, 71, 2000) has been reported so far.

However, the substance production systems by transformed plants have above superior properties, whereas their production efficiency is inferior to that of culture systems of microorganisms or mammal cells which are the current mainstream, particularly, the production efficiency by plant storage organs was low. In order to solve this problem, measures are variously being devised to enhance the ability of producing substances in transformed plants. For instance, in order to improve the ability of producing substances in one of the storage organ, i.e. a seed, from the point of view to enhance the expression of the introduced intended gene and accumulation of a gene product, studies regarding: utilization of a promoter of a plant storage protein expressed intensively in seeds (e.g. T. Katube et al., Plant. Physiol., 120, 1063, 1999), concomitant use of this promoter and a transcription factor which acts on the promoter to enhance expression (e.g. D. Yang et al., Proc, Nathl. Acad. Sci. USA., 98, 11438, 2001), insertion of 5' end untranslated region (e.g. Japanese Laid-Open Patent Application No. 2002-58492), optimization of C+G content in a gene (H. Horvath et al., Proc. Nathl. Acad. Sci. USA., 97, 1914, 2000), addition of tranduction signals to an endoplasmic reticulum (Japanese Laid-Open Patent Application No. 2000-504567), and so on have been performed energetically. It is also reported that the production amount of a foreign gene product in the seed was increased by using a mutant being deficient in a seed storage protein as a plant into which a foreign gene is introduced (Japanese Laid-Open Patent Application No. 2002-58492). However, these improvements have not provided enough substance production ability in seeds, so that development of a novel procedure has been longed.

On the other hand, a GLP-1 (glucagon-like peptide-1) is known as a hormone which is secreted from a digestive tract by food intake and acts on the pancreas to stimulate glucose-dependent insulin secretion. In Type 2 diabetic patients, it is reported that responsiveness to this GLP-1 is maintained, while the production of GLP-1 is impaired. It is expected that development of a GLP-1 agent will lead to the application of the agent to a therapeutic agent for diabetes as an insulin secretion promoter to compensate the lack of the GLP-1. However, the active substance of the GLP-1 is a polypeptide of the GLP-1 (7-36) amide or the GLP-1 (7-37), which are digested and degraded by a digestive enzyme in the gastrointestinal tract and is not absorbed sufficiently, when the GLP-1 is taken orally. Therefore, in the present state, intravenous injection and subcutaneous injection are attempted in clinical practice. Moreover, it is also reported that: the GLP-1 is also subjected to degradation by a dipeptidylpeptidase IV (DPP-IV) which exists in blood and tissues, so the active half-life time of the GLP-1 is so short as 1-2 min, and GLP-1 is easily excreted from the kidney, so its half-life time in blood is within 5 min, all of which prevents the GLP-1 from clinical application.

Hence, a GLP-1 derivative with a long half-life which is not easily degraded has been developed. For instance, followings are included: the $8^{th}$ position of amino acid substituted derivative (diabetologia 41, 271-278, 1998, Biochem 40, 2860-2869, 2001), an amino acid modulator at N— and C-terminals (WO9808871 etc.), a derivative in which Arg is substituted at its $34^{th}$ position and its $26^{th}$ position of Lys is introduced with lipophilic group (WO0007617), and a derivative by amino acid substitution covering all over the sequence (WO9943705 and WO9111457). Further, development of a sustained-release injection preparation which is subcutaneously absorbed slowly, or development of an injection preparation with synthetic Exendin-4 having a GLP-1 like agonist activity and derived from lizard whose half-life time in blood is long, have been performed. However, as they are injection preparations, considering the burden to patients, a novel GLP-1 derivative administered via an alternative route other than injection has been longed.

The object of the present invention is to provide a method for producing a plant storage organ in which a recombinant protein is highly produced, a plant storage organ in which the recombinant protein produced by the method is highly produced, and a novel derivative of a human glucagon-like peptide-1 (GLP-1) which is peptidase-resistant and the use thereof.

In order to enhance substance production in a storage organ of a transformed plant, various attempts have been performed as described above. However, in order for a plant storage organ to function in vivo sufficiently by taking it in which the recombinant protein being useful as pharmaceuticals is produced as food, it is necessary to develop a method for producing a plant storage organ in which the recombinant protein is more highly produced. In the meantime, when the recombinant protein is extracted from plants and processed as pharmaceuticals or functional food, it is important that the recombinant protein is highly produced in these storage organs on the cost front. Therefore, one of the objects of the present invention is to provide a novel method for producing a storage organ in which the recombinant protein is highly produced in transformed plants.

Meanwhile, when a GLP-1 is selected as a recombinant protein which is highly produced in a plant storage organ by said method, a therapeutic effect for diabetes can be expected by merely taking fruits, rice, and so on as normal diet. However, as mentioned above, since this native GLP-1 is digested and degraded by the digestive enzyme in the gastrointestinal tract, it can not be orally administered stably, there is no efficient method for administration except injection in the current status. It can be thought that if the GLP-1 can be passed through stomach without being digested using some method, it is absorbed in the small intestine. However, the GLP-1 must exist as a simple substance when it is absorbed. In that time, a native GLP-1 would lose activity by degradation by an enzyme such as trypsin.

Moreover, as the native GLP-1 is continuously degraded by dipeptidylpeptidase IV even after absorption, a sustained effect cannot be expected. Accordingly, in order to obtain a pharmaceutical effect from oral administration of the GLP-1, it is necessary to design a GLP-1 derivative which is not easily degraded with trypsin or dipeptidylpeptidase IV by amino acid substitution and has the sustained activity.

Therefore, one of the other objects of the present invention is to provide a novel GLP-1 derivative which is resistant to a digestive enzyme such as trypsin and can be administered orally, more preferably, a novel GLP-1 derivative which is resistant to dipeptidylpeptidase IV as well. To accomplish this object, it is required to obtain a GLP-1 derivative which is absorbed when taken as food, and which shows a pharmaceutical effect.

DISCLOSURE OF THE INVENTION

The present inventors have made a keen study concerning a method for producing a storage organ in which a recombinant protein is highly produced in a transformed plant, as a result they found that a storage organ in which a recombinant protein is highly produced in a transformed plant can be produced, through following steps: constructing a vector which comprises a recombinant protein gene to be expressed in a plant storage organ, a cytokinin-related gene, a drug-resistant gene, and a removable DNA element, where the cytokinin-related gene and the drug-resistant gene exist in the positions so that they can behave together with the removable DNA element, while the recombinant protein gene to be expressed in the plant storage organ exists in the position so that it would not behave together with the removable DNA element, introducing the vector into cells, redifferentiating a transformant from the plant cell into which the gene is introduced, and obtaining a storage organ from the redifferentiated transformant. The present invention has been thus completed.

The present invention is to apply the method for producing a plant storage organ in which a recombinant protein is highly produced to a GLP-1 known as a hormone stimulating glucose-dependent insulin secretion and to generate a GLP-1 derivative to provide the GLP-1 derivative which is not digested or degraded by a digestive enzyme and so on, and further which is stable in a blood plasma. In other word, the present inventors found that a GLP-1 derivative in which glutamine and asparagine or asparatic acid respectively are substituted at the $26^{th}$ and $34^{th}$ positions; in a peptide comprising GLP-1 (7-36) or its amino acid sequence in which one or a few amino acids are deleted, substituted and/or added and having GLP-1 activity, maintains activity at the same level as the native GLP-1, is resistant to the digestive enzyme such as trypsin, and can be absorbed from the small intestine. Further, the present inventors found that the GLP-1 derivative also obtains resistance to dipeptidylpeptidase IV and is stable also in the blood plasma by substituting serine or glycine for alanine at the $8^{th}$ position, and thus completed the present invention. In addition, the peptide is degraded by pepsin in the stomach when it is orally administered, so it was conventionally impossible to administer the peptide orally. By producing the peptide in the plant storage organ of the present invention, however, pepsin-resistance can be obtained so that oral administration can be performed.

BRIEF DESCRIPTION OF THE DRAWINGS

FIG. 8 shows comparison of the concentration dependency of cyclic AMP production activity between trypsin treated [$Gln^{26}$, $Asn^{34}$]-GLP-1 (7-36 amide) and untreated [$Gln^{26}$, $Asn^{34}$]-GLP-1 (7-36 amide) after treating with trypsin according to the method shown in Example 3 in the Examples of the present invention.

FIG. 9 shows comparison of the stability to pepsin using a GLP-1 derivative derived from polished rice of ripe seeds of *Oryza sativa* obtained in Example 1 and the powder thereof, GLP-1 (7-36 amide) (native GLP-1) in the Comparative Production Example 1, [$Ser^8$, $Gln^{26}$, $Asp^{34}$]-GLP-1 (7-36) in the Production Example 2, and [$Ser^8$, $Gln^{26}$, $Asn^{34}$]-GLP-1 (7-36) in the Production Example 3 according to the method shown in Example 4 in Examples of the present invention.

FIG. 12 shows the comparison of the DPP-IV resistance using GLP-1 (7-36 amide) (native GLP-1) in the Comparative Production Example 1, [Ser$^8$, Gln$^{26}$, Asp$^{34}$]-GLP-1 (7-36) in the Production Example 2, and [Ser$^8$, Gln$^{26}$, Asn$^{34}$]-GLP-1 (7-36) in the Production Example 3 according to the method shown in Example 7 in the Examples of the present invention.

FIG. 13 shows the comparison of the insulin secretion-promoting activity using GLP-1 (7-36) (native GLP-1 amide) in the Comparative Production Example 1, [Ser$^8$, Gln$^{26}$, Asp$^{34}$]-GLP-1 (7-36) in the Production Example 2, and [Ser$^8$, Gln$^{26}$, Asn$^{34}$]-GLP-1 (7-36) in the Production Example 3 according to the method shown in Example 8 in the Examples of the present invention.

BEST MODE OF CARRYING OUT THE INVENTION

Figure 1:
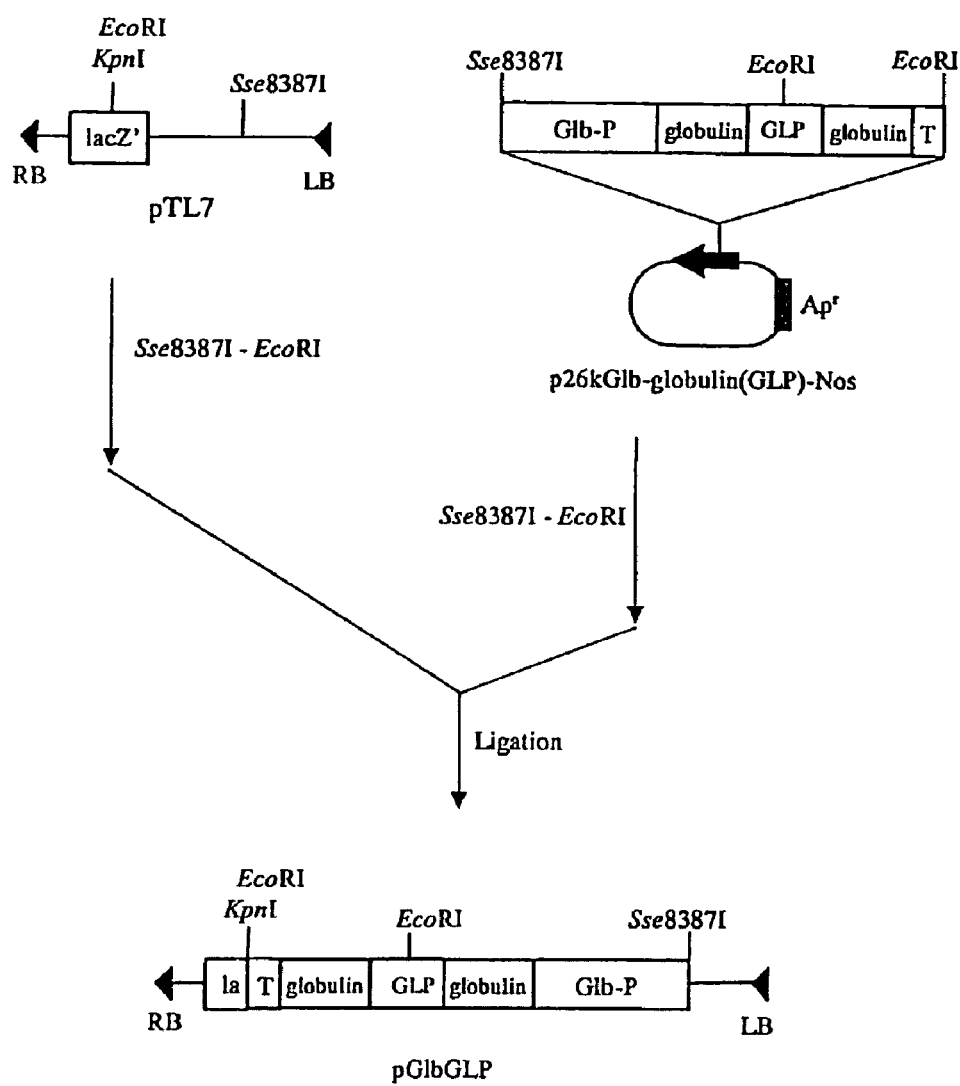
FIG. 1 shows preparation of pTL7 to pGlbGLP in the skim for preparing pGlbGLP130Hm in the Examples of the present invention.
Figure 2:
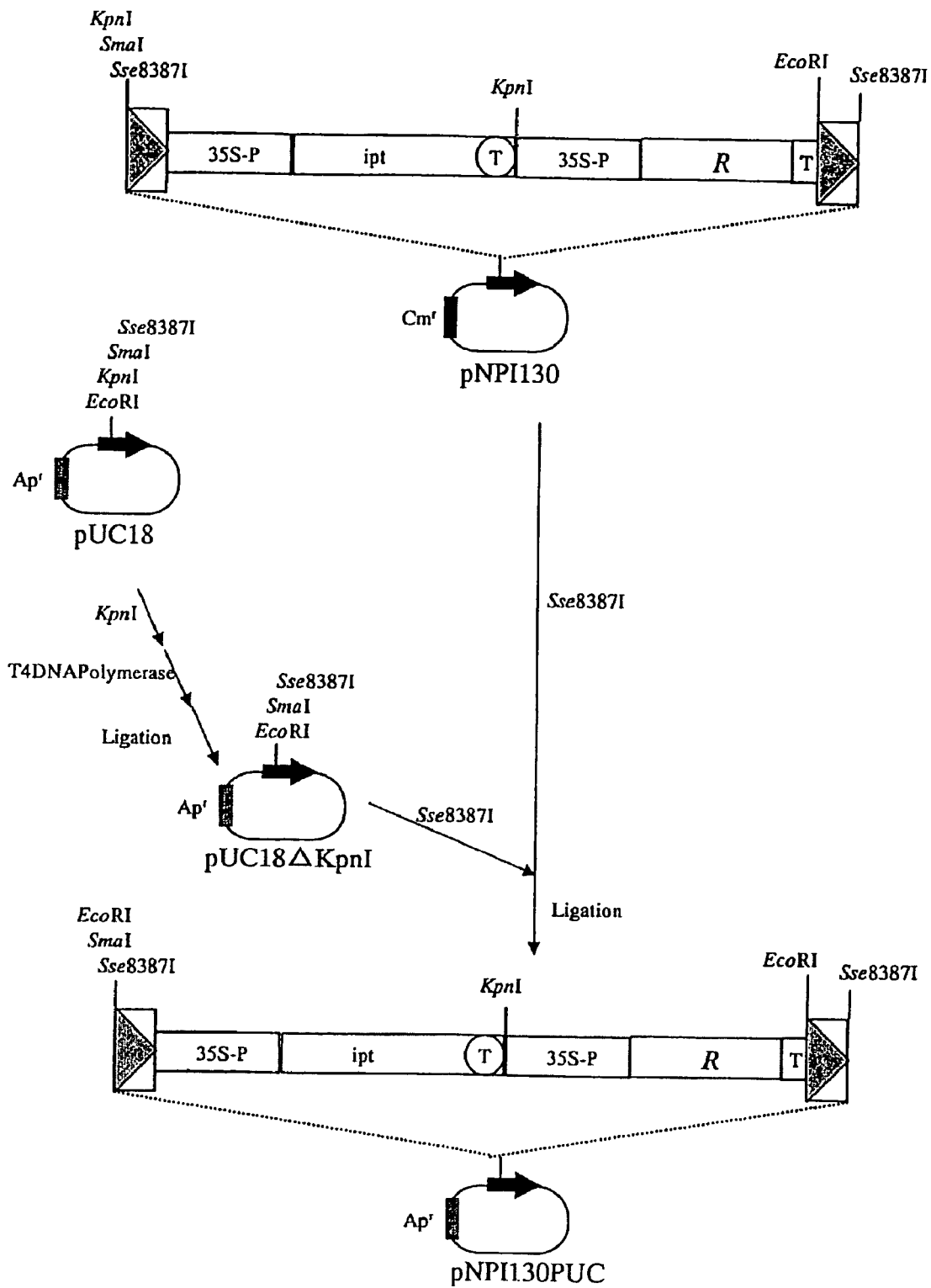
FIG. 2 shows preparation of pUC18 and pNPI130 to pNPI130PUC in the skim for preparing pGlbGLP130Hm in the Examples of the present invention.
Figure 3:
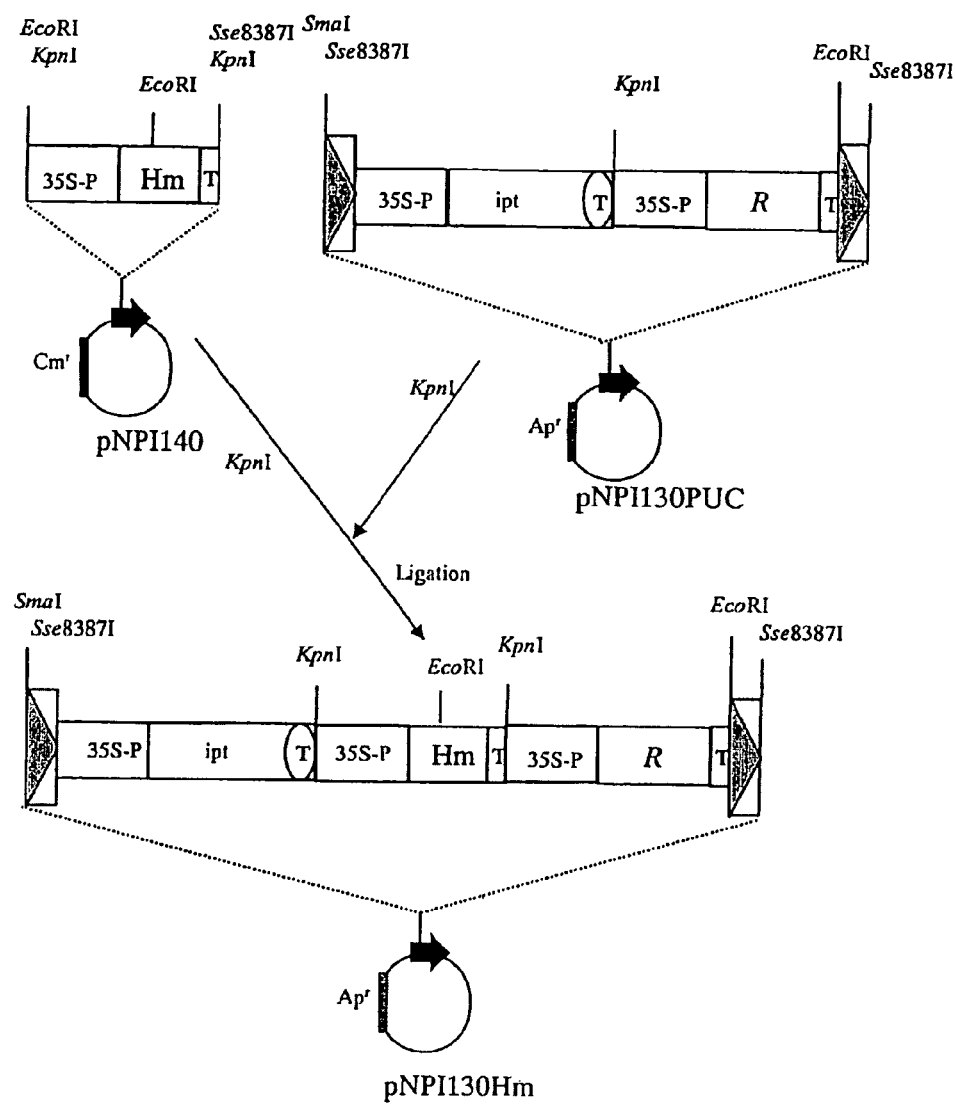
FIG. 3 shows preparation of pNPI140 and pNPI130PUC to pNPI130Hm in the skim for preparing pGlbGLP130Hm in the Examples of the present invention.

[Production of a Plant Storage Organ in Which Recombinant Protein is Highly Produced]

The present invention is a method for producing a plant storage organ in which a recombinant protein is highly produced, comprising the following steps of (A), (B), and (C): (A) constructing a vector which comprises a recombinant protein gene to be expressed in a plant storage organ, a cytokinin-related gene, a drug-resistant gene, and a removable DNA element, where the cytokinin-related gene and the drug-resistant gene exist in the positions so that they can behave together with the removable DNA element, while the recombinant protein gene to be expressed in the plant storage organ exists in the position so that it would not behave together with the removable DNA element, and introducing the vector into cells, (B) redifferentiating transformant by culturing the plant cells into which the vector introduced by said step (A) in a drug-supplemented medium and a drug-free medium, and (C) obtaining a plant storage organ from the transformant redifferentiated in said step (B). The present invention will be described in detail below.

(Subject Plants)

With regard to subject plants used in the production of the plant storage organ in the present invention, it is not specifically limited to as long as a storage organ is formed in the plant, but as dicotyledon, Nicotiana tabacum, Brassica rapa var. nippo-oleifera, and Glycine max, while as monocotyledon grains such as Oryza sativa, Zea mays, Hordeum vulgare, and Triticum aestivum, and Asparagus officinalis can be represented. Further, with regard to a plant storage organ in which the recombinant protein is highly produced in the present invention, it is not specifically limited to but a fruit, a tuberous root, a tuber, a seed, and the like can be represented.

(Genes to be Used)

Genes to be used in the present invention can be obtained by cloning of cDNA or genomic DNA. When the DNA sequence has been elucidated in advance, it maybe obtained by chemosynthesis. Further, though the DNA sequence has not been elucidated, if the amino acid sequence has been revealed, DNA sequence deduced from the amino acid sequence can be produced by chemosynthesis.

In the present invention, according to the need, the sequence of the promoter and/or the terminator necessary for gene expression is linked to the signal sequence to transfer the gene product to a storage organ efficiently and used as a gene. These sequences of the promoter, the terminator, and the signal can be used without limitation as long as they function in plants. As for this type of promoter, e.g. 35S promoter of cauliflower mosaic virus (J. T. Odell et al., Nature (London), 313, 810, 1985), the promoter of nopaline synthase (W. H. R. Langridge et al., Plant Cell Rep., 4, 355, 1985) and the like can be used. Further, use of an inductive promoter controls gene expression.

A number of such inductive promoters have been known so far. For instance, as for promoters which are induced by responding to chemical substances, followings are known: a promoter of a glutathione-S-transferase I gene (Japanese Laid-Open Patent Application No. 5-268965), a promoter of a glutathione-S-transferase II gene (International Publication WO93/01294), a Tet-repressor fusion cauliflower mosaic virus 35S promoter (C. Gatz et al., Mol. Gen. Genet., 227, 229, 1991), a Lac operator/repressor promoter (R. J. Wilde et al., The EMBO Journal, 11, 1251, 1992), an alcR/alcA promoter (International Publication WO94/03619), a glucocorticoid promoter (Aoyama, PROTEIN, NUCLEIC ACID AND ENZYME, 41: 2559, 1996), and a par promoter (T. Sakai et al., Plant Cell Physiol., 37, 906, 1996). As promoters which are induced by responding to light, followings are known: a promoter of a ribulose diphosphate carboxylase small subunit gene (rbcs) (R. Fluhr et al., Proc. Natl. Acad. Sci. USA, 83, 2358, 1986), a promoter of a fructose-1,6-bisphosphatase gene (Japanese Patent Publication No.7-501921), a promoter of a light-harvesting chlorophyll a/b binding protein gene (Japanese Laid-Open Patent Application No. 5-89) and the like. Other than above, promoters which are induced by responding to various external environments such as injury, temperature and the like, are known.

As for a promoter, for the recombinant protein gene of the present invention, an inductive promoter and a promoter showing constant expression such as a 35S promoter can be used as described above, but it is particularly desirable to use a promoter specific to the plant storage organ, since the expression of the promoter specific to the plant storage organ is guaranteed to be expressed in the plant storage organ in which the recombinant protein gene is attempted to be produced. Thus, the promoter which promotes specific expression in certain tissue or organ in plants is also known to the skills in the art widely. For instance, in the present invention, as for the promoter, a promoter of a globulin gene (M. Nakase et al., Plant Mol. Biol., 33, 513, 1997), a promoter of a glutelin gene (F. Takaiwa et al., Plant Mol. Biol., 17, 875, 1991), and the like can be used, which are promoters of seed storage protein genes which express foreign genes in seeds of *Oryza sativa*. Further, promoters of seed storage protein genes of major crops such as a promoter of a glycinin gene, a promoter of a glusiferrin gene (J. Rodin et al., plant Mol. Biol., 20, 559, 1992), and the like can also be used, which are promoters expressing foreign genes in seeds of Fabaceae crops such as *Phaseolus vulgaris, Vicia faba, Pisum sativum*, and so on and seeds of oil seed crops such as *Arachis hypogaea, Sesamum indicum, Brassica rapa* var. *nippo-oleifera, Gossypium arboreum, Helianthus annuus, Carthamus tinctorius L.*, and so on.

On the other hand, in the present invention, terminators of the plant genes registered in DNA data base including a terminator of a nopaline synthase (A. Depicker et al., J. Mol. Appl. Gen., 1, 561, 1982), and a terminator of octopine synthase (J. Gielen et al., EMBO J., 3, 835, 1984) can be selected variously and used.

In the present invention, the recombinant protein gene which can be introduced into a plant may not only be a gene encoding a functional or medical peptide capable of contributing to the health of human and animal such as livestock, but also be a gene encoding an optional peptide or protein whose functional is unknown. For instance, in the Examples of the present invention, the gene encoding a GLP-1 derivative was introduced into plant and the GLP-1 derivative was produced in the plant seed, but the recombinant protein which can be produced in the plant storage organ according to the procedure of the present invention is not limited to the GLP-1 or the derivative thereof, and various peptides and proteins such as: various peptides or proteins having been used or developed as pharmaceuticals already (S. Josephson and R. Bishop, TIBTECH, 6, 218, 1998), a recently found hypocholesterolemic peptide (e.g. Japanese Laid-Open Patent Application No. 2001-114800), a T-cell epitope peptide of tick or pollen antigen (e.g. U.S. Pat. No. 6268491, Japanese Laid-Open Patent Application Nos. 10-7700, 10-259198, 10-506877, 11-92497, and 2000-327699), and the like, can be produced in a plant storage organ according to the procedure of the present invention.

Additionally, these peptides may be produced with suitable modification according to the nature and the object. That is, as exemplifying the GLP-1, other than the GLP-1, the present invention can be applied to the peptide comprising a GLP-1 (7-36) or its sequence in which one or a few amino acids are deleted, substituted and/or added and having GLP-1 activity, or a GLP-1 derivative comprising an amino acid sequence in which glutamine and asparagine or aspartic acid are respectively substituted at the $26^{th}$ and $34^{th}$ positions of the peptide. Further, the present invention can also be applied to a GLP-1 derivative whose peptide, which comprises a GLP-1 (7-36) or its sequence in which one or a few amino acids are deleted, substituted and/or added and which has GLP-1 activity, is GLP-1 (7-36), GLP-1 (7-37), or C-terminal amide of GLP-1 (7-36) or GLP-1 (7-37). Moreover, the present invention can also be applied to the GLP-1 derivative in which serine or glycine is substituted at the $8^{th}$ positions of these GLP-1 derivatives, and the GLP-1 derivative shown in SEQ ID NO: 2 in the sequence listing.

(Construction of Recombinant Protein Gene to be Introduced)

In the present invention, a fusion gene produced by: inserting the gene (DNA sequence) encoding these recombinant proteins into genetic sequence encoding the variable region which does not negatively affected on accumulation or the like of the protein in the protein gene such as seed storage protein originally expressed in the plant storage organ in which recombinant protein is to be highly produced according to the procedure of the present invention, or by substituting for the gene, can be used. For instance in Examples, the gene encoding the above GLP-1 derivative was inserted into the position to encode the protein variable region in a globulin gene, and used as a fusion gene. At the same time, by aligning an enzyme fragmentation sequence at the boundary between the recombinant protein gene and the reserve protein gene which is originally expressed in the plant storage organ where the recombinant protein gene is inserted or substituted for, the object recombinant protein can be cleaved and purified after the expression product of the fusion gene is extracted and treated with the enzyme. Further, aligning the cleaved sequence by a digestive enzyme such as trypsin there, the object peptide or protein is cleaved in the small intestine and absorbed into body after the plant storage organs such as seeds in which the recombinant protein is highly produced by the procedure of the present invention is taken as food, which leads that various physiological functions are exerted.

Meanwhile, the seed storage protein is a protein stored mainly in a seed, and has an important function as nutrient necessary for germination (Science of the Rice Plant vol. 3, Rural Culture Association). The type of the seed storage protein gene which can be used in the present invention is not specifically limited to, for instance, a gene such as of globulin, glutelin, and prolamin of *Oryza sativa*, and 2s albumin of *Arabidopsis thaliana* (Japanese Laid-Open Patent Application No. 2000-106890) can be used. Further, insertion position of the recombinant protein gene is not specifically limited to as long as it is a variable region which does not change the property of the protein which is originally encoded by the seed storage protein gene. For instance, in Examples of the present invention, a gene encoding the GLP-1 derivative was inserted into the position which encodes $109^{th}$ amino acid position of rice globulin.

(Construction of the Introducing Vector)

In the present invention, a gene is introduced into a plant by the vector constructed so that the cytokinin-related gene and the drug-resistant gene exist in the positions so that they can behave together with the removable DNA element, while said recombinant protein gene exists in the position so that it would not behave together with the removable DNA element.

Here, the cytokinin-related gene is referred to as a gene involved in production of cytokinin and so on which has functions causing promotion of cell division in a plant, differentiation of a definite bud or an adventitious bud from the plant tissue, or the like.

As for the cytokinin-related gene, other than an ipt gene derived from *Agrobacterium tumefaciens* (hereinafter abbreviated as *A. tumefaciens*) (A. C. Smigocki, L. D. Owens, Proc. Natl. Acad. Sci. USA 85, 5131, 1988), an ipt gene derived from *Rhodococcus*, a cytokinin synthase gene derived from *Arabidopsis thaliana*, and a cytokinin synthase gene such as a ptz gene derived from *Pseudomonas*, any of cytokinin-related genes of a β-glucuronidase gene derived from *E. coli* which is a gene activating inactive cytokinin (Morten Joersbo and Finn T. Okkels, Plant Cell Reports 16, 219-221, 1996), and a CK11 gene derived from *Arabidopsis thaliana* thought as a cytokinin-receptor gene (Kakimoto T. Science 274, 982-985, 1996), can be used in the present invention.

Further, in the present invention, the drug-resistant gene is referred to as a gene which confers antibiotic resistance or pesticide resistance to the plant cell into which the drug-resistant gene is introduced. As for the antibiotic-resistant gene, a hygromycin-resistant gene (HPT: a hygromycin phosphorylated enzyme gene), a kanamycin-resistant gene (NPTII: a neomycin phosphorylated enzyme gene), and the like can be used for example, while as for the pesticide-resistant gene, a sulfonylurea-resistant gene (ALS; an acetolactate synthase gene) and the like can be used.

The removable DNA element is referred to as a DNA sequence which has an ability to remove from the chromosomal DNA or the like where it exists and functions. In plants, what is called transposon existing on chromosomal DNA has been known as one of these elements, whose structure, function, and behavior have been almost elucidated. In other words, in order for transposon to function, two constituents are required in principle: an enzyme which expresses from the gene existing therein and catalyzes removement and transfer of the enzyme per se (transferase), and the DNA sequence also exists in the terminal region therein and to which the transferase binds and on which it acts. By these functions, transposon removes from the chromosomal DNA on which it exists, and it generally transfers to the new position on the DNA, however, there is a case that the transposon loses its function without transferring and disappears at a constant rate, therefore such transferring error of transposon is used in the present invention.

Meanwhile, with regard to the transposon, other than such autonomous transposon which possesses two constituents of transferase and DNA binding sequence and can remove autonomously from the chromosome on which is it exists by the action resulted from binding transferase which expresses from inside of transposon to the DNA sequence existing at terminal region, and then it can transfer, there is also a type called as nonautonomous transposon. This nonautonomous transposon is referred to as the one which possesses the DNA sequence at the terminal to which transferase binds and on which it acts, though it cannot remove autonomously from the chromosome due to lack of transferase expression caused by mutation of the transferase gene therein. However, when the transferase is provided from the autonomous transposon or the transferase gene exists independently of it, the nonautonomous transferase shows behavior similar to that of the autonomous transposon.

With regard to the autonomous transposon, there is Ac, Spm, and the like which are isolated from Zea mays (A. Gieri and H. Saedler, Plant Mol. Biol., 19, 39, 1992). Especially, Ac can be obtained by cleaving a wx-m7 gene locus in the chromosome of Zea mays with a restriction enzyme Sau3A (U. Behrens et al., Mol. Gen. Genet. 194, 346, 1984), it is the autonomous transposon which is the most analyzed plant transposon and its DNA sequence has already been elucidated (M. Muller-Neumann et al., Mol. Gen. Genet., 198, 19, 1984), and the skilled in the art can obtain it easily, therefore, it is suitable for the DNA element used in the present invention. Further, with regard to the nonautonomous transposon, including Ds and dSpm in which the internal regions of Ac and Spm are deleted, respectively (H.-P. Doring and P. Starlinger, Ann. Rev. Genet. 20, 175, 1986), the nonautonomous transposon isolated from variety of plants such as Antirrhium majus, Pharbitis nil, etc. other than Zea mays (e.g. Y. Inagaki et al., Plant Cell, 6, 375, 1994), are known.

Incidentally, such transposon has been known from many examples that even if it is introduced into the plant chromosome whose species is different from the one from which it is derived; it exerts its ability to remove and transfer (e.g. B. Baker et al., Proc. Natl. Acad. Sci. USA, 83. 4844, 1986). Meanwhile, in the present invention, either autonomous or nonautonomous transposon can be used. When the nonautonomous transposon is used, the transferase gene obtained from autonomous transposon or synthesized and so on is required to be introduced in addition to the nonautonomous transposon, in such a case, it may be introduced by integrating with this nonautonomous transposon into the vector of the present invention, or they may be introduced completely independently.

Further, as a removable DNA element existing in other than plants, the one derived from a site-specific recombination system is known. The site-specific recombination system comprises two constituents: a recombination site (which is equal to the removable DNA element of the present invention) having a characteristic DNA sequence, and an enzyme which specifically binds to the DNA sequences and catalyzes recombination between the sequences when there are two or more of the sequences. The DNA element shows behavior when the DNA sequences exist at two positions at a regular interval in the same direction on the same DNA molecule, the region between the sequences is removed from this DNA molecule (a plasmid, a chromosome or the like), while when the sequences exist at two positions in the opposite direction, the region is inverted. In the present invention, the removing action of the former is utilized. Meanwhile, a gene encoding a recombinant enzyme does not necessarily exist on the DNA molecule the same as that of the recombination site, it is known that it can cause remove and inversion between the DNA sequences as long as it only exists and expresses in the same cell (N. L. Craig, Annu. Rev. Genet., 22, 77, 1998).

Currently, a Cre/lox system, a R/RS system, a FLP system, a cer system, a fim system, and soon isolated from microorganisms such as a phage, a bacteria (e.g. *E.coli*), and yeast are known as a site-specific recombination system (general statement in N. L. Craig, Annu. Rev. Genet., 22, 17, 1998), although it has not been confirmed whether the site-specific recombination system exists in higher organisms. However, even when the site-specific recombination system is introduced into the species of organism different from the species such as plant from which it is derived, it has been revealed that the site-specific recombination system isolated from these microorganisms behaves in the same manner as it does in the organism from which it is originally derived, as the Cre/lox system derived from P1 phage is used for the transgenic vector for introducing into plants in International Publication WO93/01283. Incidentally, in one Example of the present invention, the R/Rs system (H. Matsuzaki et al., J. Bacteriology, 172, 610, 1990), the site-specific recombination system of yeast (*Zygosaccharomyces rouxii*), was used by inserting a recombinant enzyme between the recombination sites, it has already been reported that the R/Rs system also maintains the original function in higher plants (H. Onouchi et al., Nucleic Acid Res., 19, 6373, 1991).

In the present invention, there is no limitation of the position to insert the cytokinin-related gene and the drug-resistant gene into, as long as it is the position where they can remove with the removable DNA element. For instance, the autonomous transposon is used as a removable DNA element, it can be inserted into the position which does not affect remove of transposon at the upstream from the promoter region of a transferase gene and the downstream from the terminal region to which the trasnferase gene binds. When the R/RS system is used, it can be inserted into any position, as long as it is the position which does not inhibit the expression of the recombinant enzyme, and is in the region between the recombination sites.

(Introduction of the Constructed Vectors Into Plant Cells)

In the present invention, thus constructed vector is introduced into plant cells. With regard to the plants into which the vector is introduced, as described in the above (subject plants) section, it is not specifically limited to as long as it is a plant forming a storage organ, but grains such as *Oryza sativa, Zea mays, Hordeum vulgare*, and *Triricum aestivum*, and *Asparagus officinalis* as monocotyledon, and *Nicotiana tabacum, Brassica rapa. nippo-oleifera*, and *Glycine max* as dicotyledon, can be exemplified as representative plants. In addition, the constructed vector can be introduced into a plant cell by using the known method. Besides the method using genus agrobacterium, any known method such as electroporation method, polyethylenglycol method, and particle gun method can be used, and it is not specifically limited to.

When the recombinant protein gene is introduced into *Oryza sativa* by using the method of the present invention, for example, the method described in Japanese Patent No.3141084 is preferably used. Here, with regard to the plating medium for plating a *Oryza sativa* seed and germinating it, for instance an N6C12 medium (N6 inorganic salts and vitamins (Chu C. C., 1978, Proc. Symp., Plant Tissue Culture, Science Press Beijing, 43-50), 30 g/L sucrose, 2.8 g/L proline, 0.3 g/L casamino acid, 1 mg/L 2,4-D, 4 g/L GelRite) can be used. However, the medium composition is not specifically limited to the above mentioned one, and the present invention can also be carried out by modifying the type or concentration of the composition.

(Redifferentiation of the Transformant)

When the transformant from the plant cell or tissue introduced with the recombinant protein gene is redifferentiated, the cell or tissue introduced with the gene may be cultured by using the known method in a drug-supplemented medium and a drug-free medium. Meanwhile, the transformant in the present invention is referred to as a plant tissue such as a definite bud, an adventitious bud, and an adventitious root or a seedling plant.

For instance, for obtaining a transformant by introducing the recombinant protein gene into *Oryza sativa* according to the present invention, the transformant can be obtained as a bud or a seedling plant by following procedures: cleaving the scutellum tissue of *Oryza sativa* out of the geminated seed introduced with the gene according to the method described in Japanese Patent No. 3141084 by using the vector constructed as above-mentioned, culturing the scutellum tissue for one week in a medium such as a drug-supplemented medium N6C12TCH25 medium (N6 inorganic salts and vitamins, 30 g/L sucrose, 2.8 g/L proline, 0.3 g/L casamino acid, 2 mg/L 2,4-D, 500 mg/L carbenicillin, 25 mg/L hygromycin, and 4 g/L GelRite), further culturing it for one week in a drug-supplemented medium N6C14TCH25 medium (N6 inorganic salts and vitamins, 30 g/L sucrose, 2.8 g/L proline, 0.3 g/L casamino acid, 4 mg/L 2,4-D, 500 mg/L carbenicillin, 25 mg/L hygromycin, and 4 g/L GelRite), and then culturing it in a drug-free medium MSRC medium (MS inorganic salts and vitamins (Murashige, T. and Skoog, F., 1962, Physiol. Plant., 15, 473), 30 g/L sucrose, 30 g/L sorbitol, 2 g/L casamino acid, 500 mg/L carbenicillin, and 4 g/L GelRite). The culture condition exemplified above is not the absolute requirement, therefore, the type or concentration of the medium composition can be modified, various plant hormones or agents can be added to the medium, and culture period can be modified according to the need without mentioning.

Meanwhile, with regard to the drug-supplemented medium, the medium to which the drug suitable for the drug-resistant gene integrated into the vector constructed as described above and used for gene introduction is added. For example, the medium to which hygromicin, kanamycin, and sulfonylurea pesticide are added may be used when a hygromycin-resistant gene, a kanamycin-registant gene, and a sulfonylurea-resistant gene are integrated into this vector, respectively.

(Obtaining a Plant Storage Organ)

In the present invention, a plant storage organ may be obtained by redifferentiating the transformant as described above from the plant cell or organ into which the recombinant protein gene is introduced, and then growing the transformant with the use of the known method. For instance, when the transformant is an adventitious bud, a storage organ such as a plant maturing seed in which the recombinant protein is highly produced may be harvested after performing rhizogenesis treatment to regenerate the plant individual and growing the plant individual to fructify, according to the known method. Meanwhile, rhizogenesis of an adventitious root can be performed by the method such as incorporating an adventitious bud into an MS agar medium. In addition, when the transformant is obtained as a seedling plant, the transformant plant can be obtained without performing rhizogenesis treatment or the like. Further, when a tuberous root, a tuber, or the like is used as a plant storage organ, it also can be obtained by differentiating these tissues by the known means from the obtained transformant without going through the generation process of the plant individual.

(Production of the GLP-1s)

In the present invention, the GLP-1s are provided by using the method for producing the plant storage organ in which the recombinant protein is highly produced of the present invention. The GLP-1 is known as a hormone stimulating glucose-dependent insulin secretion, while GLP-1 (7-36) is a peptide having a sequence shown by His-Ala-Glu-Gly-Thr-Phe -Thr-Ser-Asp-Val-Ser-Ser-Tyr-Leu-Glu-Gly-Gln-Ala-Ala-Lys-Glu-Phe-Ile-Ala-Trp-Leu-Val -Lys-Gly-Arg (SEO ID NO: 7). In the present invention, a gene encoding the amino acid sequence of the GLP-1 (7-36), or a gene encoding peptide which comprises the sequence in which one or a few amino acids are deleted, substituted and/or added in the amino acid sequence of GLP-1 (7-36) and has GLP-1 activity, is integrated as the gene expressing the above recombinant protein into the vector constructed in the present invention to express the gene and produce GLP-1s.

(GLP-1 Derivative)

The present invention is to provide the method for producing the GLP-1s as described above and to generate the GLP-1 derivative for providing the GLP-1 derivative which is not digested or degraded by a digestive enzyme and so on, and further which is stable also in a blood plasma. The derivative of the present invention was modified so that it can be absorbed from the small intestine by substituting glutamine and asparagine or aspartic acid, respectively, at the $26^{th}$ and $34^{th}$ positions in the peptide comprising the GLP-1 (7-36) or its amino acid sequence in which one or a few amino acids are deleted, substituted and/or added and having GLP-1 activity, through which the GLP-1 derivative maintained insulin secretion promoting activity at the same level as native GLP-1 and was given a resistance to the digestive enzyme such as trypsin. Further, it was modified by substituting serine or glicine for alanine at the 8$^{th}$ position so as to obtain the resistance to dipeptidylpeptidase IV as well to be stable also in the blood plasma.

That is, the GLP-1 derivative of the present invention is the peptide having an amino acid sequence in which glutamine and asparagine or aspartic acid, respectively, are substituted at the 26$^{th}$ and 34$^{th}$ positions in the peptide comprising the GLP-1 (7-36) or its sequence in which one or a few amino acids are deleted, substituted and/or added and having GLP-1 activity. Here the peptide comprising the GLP-1 (7-36) or its sequence in which one or a few amino acids are deleted, substituted and/or added and having GLP-1 activity includes a precursor and an analogue of the GLP-1 and the C-terminal amide bodies, and it is preferably the GLP-1 (7-36), the GLP-1 (7-37) or the C-terminal amide of the GLP-1 (7-36) or the GLP-1 (7-37). It is particularly preferable to substitute serine or glicine at the 8$^{th}$ position in the GLP-1 derivative of the present invention. Dipeptidylpeptidase IV is an enzyme which recognizes proline or alanine at the second site from the N-terminal of polypeptide chain and hydrolyzes the side of carboxyl group. Therefore, it is preferable to substitute serine or glicine for alanine at the 8$^{th}$ position in the GLP-1 derivative of the present invention. This derivative substitution at the 8$^{th}$ position maintains activity at the same level as that of the native GLP-1, and is stable also in a blood plasma.

As above-stated, the GLP-1 (7-36) used in the present invention is a peptide comprising the following amino acid sequence shown by the sequence: His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQ ID NO: 7), here [Ser$^8$] showing that the 8$^{th}$ position is modified by serine indicates that the second (corresponding to the 8$^{th}$ position) Ala is replaced with Ser. The GLP-1 derivative of the present invention can be produced using chemosynthesis or genetic engineering technique.

That is, the principal of chemosynthesis of polypeptide is commonly known in the art, general text of the art as following can be referred to: Dugas H. and Penny C. Bioorganic Chemistry, 1981, Springer-Verlag, NewYork, pp. 54-92, Merrifields J M, Chem. Soc, 85, 2149, 1962, Stewart and Young, Solid Phase Peptide Synthesis, pp. 24-66, Freeman (San Francisco, 1969). The peptide of the present invention can be synthesized by solid phase method with the use of e.g., 430A peptide synthesizer (PE-Applied Biosystems Inc, 850 Lincoln Center Drive, Foster City Calif. 94404) and synthesis cycle supplied by PE-Applied Biosystems. Boc amino acid and other reagents can be purchased from PE-Applied Biosystems and other pharmaceutical supplier.

Production of the GLP-1 derivative of the present invention by genetic engineering technique can also be performed with the use of the gene obtained from total synthesis of the DNA of the GLP-1 derivative or modification of DNA encoded by larger natural glucagons. The method for constructing synthetic gene is widely known in the art, and Methods in Enzymology, Academic Press, NY, vol. 68, 109-151 by Brown et al. can be referred to.

Further, DNA used for generating the GLP-1 derivative of the present invention can be designed to enhance expression amount and accumulate the product stably in the host, to facilitate the purification after production, or to produce the product as fusion protein and cleave the GLP-1 derivative out easily, other than the above-mentioned devices. For instance, to joint it to a gene of a protein such as β-galactosidase, β-lactamase, a protein A, TrpE to generate it as a fusion protein is one of these procedures. In these cases, in order to obtain the GLP-1 derivative as a simple substance after generation, a gene corresponding to methionine of amino acid can be inserted between each gene to treat it with cyanogen bromide. Here, the C-terminal is changed to Hse (homoserine). Some of the GLP-1 derivatives of the present invention have arginine only at C-terminal, so a simple substance of the GLP-1 derivative can be obtained by enzymatic treatment with an arginyl endopeptidase.

Meanwhile, the gene encoding the above GLP-1 derivative can also produce the GLP-1 derivative by being introduced into cells other than plants and being expressed according to the known genetic engineering technique. In this case, the gene encoding the GLP-1 derivative is introduced into a suitable recombinant DNA expression vector by using a suitable restriction endonuclease. After constructing an expression vector for the GLP-1 derivative, a suitable host cell is transformed by using the vector. Either eukaryotic cells or prokaryotic cells can be used as host cells. The techniques to construct a vector and to transform cells are commonly known in the art, and Molecular Cloning; A Laboratory Manual, Cold Springs Harbor Laboratory Press, NY. vols. 1-3, 1989 by Maniatis et al. can be generally referred to. In such case, in order to achieve efficient transcription of the subject gene, the subject gene is bound to the promoter-operator region functionally. Various expression vectors which can be used for transformation of eukaryotic cells or prokaryotic cells are commonly known and The Promega Biological Research Products Catalogue and The Stratagene Cloning Systems Catalogue can be referred to. In production of the GLP-1 derivative of the present invention, widely used substance production system using microorganisms and culture cells of mammals as hosts can be used. Further as a stable substance production system at low cost, a substance production system using transformed plant as described above can also be used.

[Use of the GLP-1 Derivative of the Present Invention]

The GLP-1 derivative produced in the present invention can be used by taking in the form of a storage organ such as plant seeds, in the form of a preparation by purification and isolation, or in the form of food or drink or the like to which the constituent is added. When it is used in the form of preparation, it can also be used as pharmaceuticals by combining the constituent comprising the GLP-1 derivative and pharmaceutically acceptable carrier, diluent, excipient or an absorption promoter to formulate into pharmaceuticals. The GLP-1 derivative of the present invention is effective for various diseases in which the GLP-1 is involved, so it can be used for e.g. treatment of insulin-independent chronic diabetes mellitus, treatment for insulin-dependent chronic diabetes mellitus, treatment for obesity, or appetite suppression.

EXAMPLES

The present invention is described below more specifically with reference to Examples, however, the present invention is not limited to the following Examples. Meanwhile, in the following Examples, further detailed experimental operation was performed according to the procedures of molecular biology by Molecular Cloning (Sambrook et al., 1989) or the operation manual by the manufacturer unless otherwise stated.

Example 1

I. Preparation of Plasmid pGlbGLP130Hm

Rice globulin promoter cleaved using restriction enzymes EcoRI and Sse 83871, rice globulin gene wherein a gene encoding [Ser⁸, Gln²⁶, Asp³⁴]-GLP-1 (7-36 amide) shown in SEQ ID NO:1 was inserted into the variable region (the 109$^{th}$ position of the amino acid), and a gene fragment linked to polyadenylation signal of nopaline synthase were inserted into EcoRI-Sse83871 restriction enzyme site of pTL7 (H. Ebinuma et al., Molecular Methods of Plant Analysis, 22:95, 2002), to obtain plasmid pGlbGLP. As shown in SEQ ID NO:2, [Ser⁸, Gln²⁶, Asp³⁴]-GLP-1 (7-36) comprises amino acid 7-36 of GLP-1, and is a derivative wherein the 8$^{th}$, 26$^{th}$ and 34$^{th}$ positions are replaced with serine, glutamine and asparagine, respectively. For insertion into the rice globulin gene, lysine residue (AAG) was added to its N-terminal.

On the other hand, plasmid pUC18ΔKpnI was obtained by cleaving the restriction enzyme site KpnI of plasmid pUC18 with restriction enzyme KpnI, blunting its cleavage end with T4 polymeraze, and then by re-bond. The region between recombinant sequences Rs of the yeast site-specific recombination system was cleaved from plasmid pNPI130 (Japanese Laid-Open Patent Application No.9-154580) with restriction enzyme Sse8387I and insertion into the restriction enzyme site Sse8387I of the pUC18ΔKpnI, to obtain plasmid pNPI130PUC.

Further, a gene fragment linked to the CaMV35S promoter, the Hm (hygromycin-resistant) gene and the polyadenilation signal of nopaline synthase was cleaved from the plasmid pNPI140 (Japanese Laid-Open Patent Application No.9-154580) with restriction enzyme KpnI, and inserted into the restriction enzyme site KpnI of pNPI130PUC, to obtain plasmid pNPI130Hm.

The intended plasmid was obtained by cleaving from the pNPI130Hm, the region between recombinant sequences Rs of the yeast site-specific recombination system with the restriction enzyme Sse8387I, and introducing it between the restriction enzymes site Sse8387I of pGlbGLP, and named it as plasmid pGlbGLP130Hm (International Accession No. FERM BP-8343). In the pGlbGLP130Hm, a gene encoding [Ser⁸, Gln²⁶, Asp³⁴]-GLP-1 (7-36) exists because it has been inserted into the variable region (the 109$^{th}$ position of the amino acid) of rice globulin gene, as a recombinant protein gene allowing to express in plant storage organ. Moreover, it comprises an ipt gene as a cytokinin-related gene and a hygromycin-resistant gene as a drug-resistant gene, and uses the yeast site-specific recombination system R/RS system as a removable DNA element.

Figure 4:
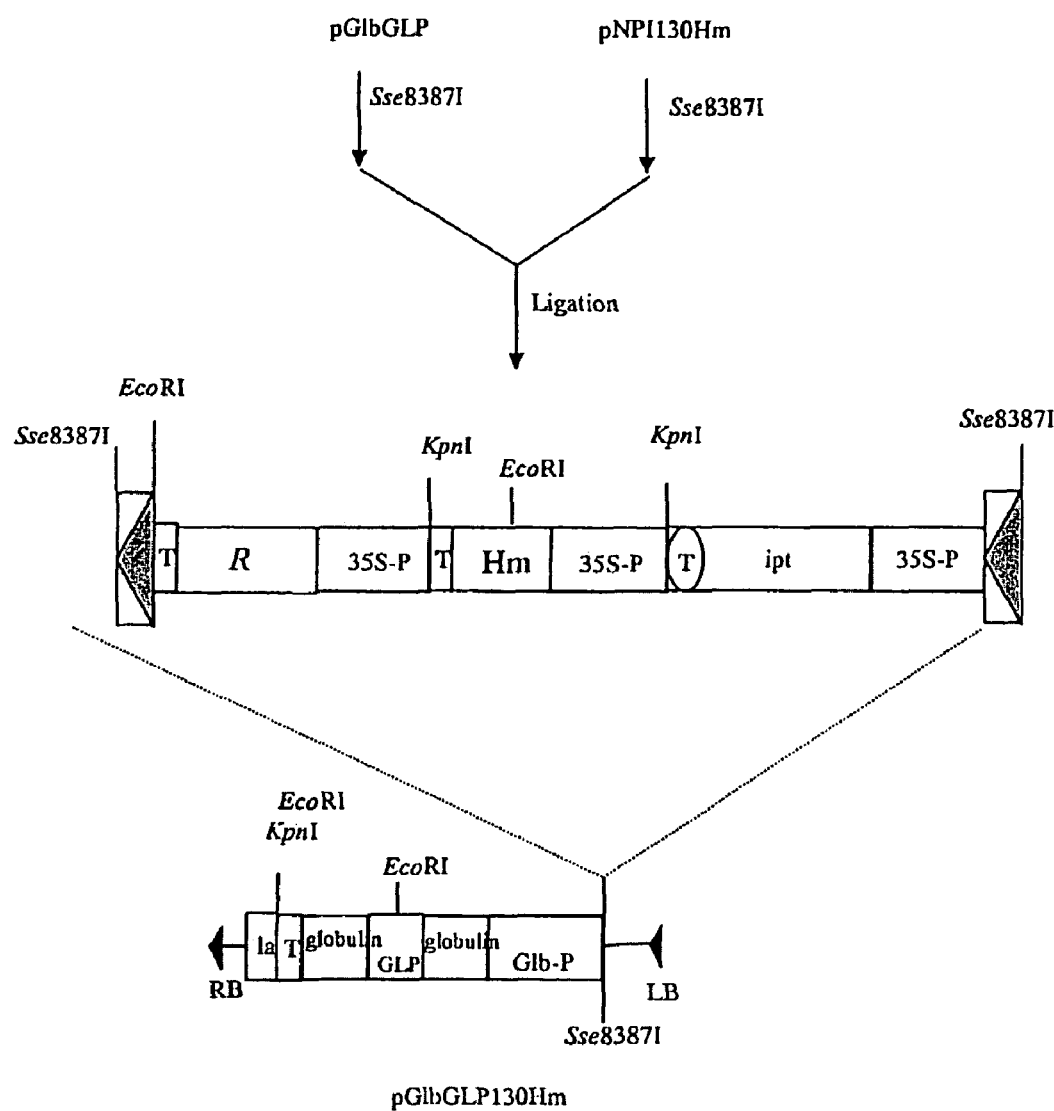
FIG. 4 shows preparation of pGlbGLP and pNPI130Hm to pGlbGLP130Hm as well as a restriction map of pGlbGLP130Hm in the Examples of the present invention.

The skims for preparing pGlbGLP130Hm are shown in FIGS. 1-4, and restriction map of the region (T-DNA region) in pGlbGLP130Hm to be integrated into plant chromosome is shown in FIG. 4. In FIGS. 1-4, Glb-P represents a promoter of globulin gene; GLP represents a gene encoding [Ser⁸, Gln²⁶, Asp³⁴]-GLP-1 (7-36); globulin represents rice globulin gene; T represents polyadenylation signal of nopaline synthase gene; la represents fragment of lacZ' gene; 35S-P represents 35S promoter of cauliflower mosaic virus; ipt represents an ipt gene; circled-T represents polyadenylation signal of ipt gene itself; Hm represents hygromycin resistant gene; R represents recombinant enzyme gene; triangle framed with a rectangle represents recombinant sequence Rs and its sequence direction; and RB and LB represent boundary sequences of T-DNA region.

II. Introduction of pGlbGLP130Hm to *Agrobacterium*

A. tumefaciens EHA 105 strain was inoculated in 10 mL YEB liquid medium (beef extract 5 g/L, yeast extract 1 g/L, peptone 5 g/L, sucrose 5 g/L, 2 mM of MgSO4, pH 7.2 at 22° C. (hereinafter, pH will be the value at 22° C., unless otherwise stated)), and cultured at 28° C. until OD630 value reached 0.4 to 0.6. The culture liquid was centrifuged at 6900×g at 4° C. for 10 min, and harvested bacteria. Then, the bacteria was suspended in 20 ml of 10 mM HEPES (pH 8.0), centrifuged again at 6900×g at 4° C. for 10 min and harvested bacteria. The resultant bacteria were further suspended in 200 µl of YEB liquid medium, and used this as the bacterial culture for plasmid introduction.

By using the bacterial culture for plasmid introduction, the introduction of pGlbGLP130Hm into *Agrobacterium* was performed as follows. In other words, electropolation was performed with the mixed solution of 50 µl of the above bacterial culture for plasmid introduction and 3 µl of pGlbGLP130Hm with gene pulser II system (BIORAD) in a 0.5 ml-tube. Then, 200 µl of YEB liquid medium was added to the resultant mixed solution after electropolation treatment, and the mixture was cultured by shaking at 25° C. for 1 hour. The bacteria were further inoculated in YEB agar medium (agar 1.5w/v %, other components were same as above) supplemented with 50 mg/L kanamycin and cultured at 28° C. for 2 days. Further, the obtained bacteria colony was transplanted into YEB liquid medium and cultured. Then plasmid was extracted from the bacteria by alkaline method, to confirm these bacteria were EHA 105 strain introduced with pGlbGLP130Hm, and these were named as EHA 105 (pGlbGLP130Hm).

III. Preparation of Infection Material

As target of gene introduction, *Oryza sativa* variety "NIPPONBARE" was used, and the sterilization of the ripe seeds was performed according to the method of "Cell Engineering Annex, Plant Cell Engineering Series 4, Experiment Protocol of Model Plant (pp.93-98)". The sterilized ripe seeds were placed in N6C12 medium (N6 inorganic salts and vitamins, 30 g/L sucrose, 2.8 g/L proline, 0.3 g/L casamino acid, 1 mg/L2,4-D, 4 g/LGelLight, pH=5.8), sealed with surgical tape, cultured in a lighted place at 28° C. for germination, and made it an infection material by Agrobacterium EHA 105 (pGlbGLP130Hm).

IV. Transformation of Rice by EHA 105 (pGlbGLP130Hm) and Preparation of Transformed Rice

*Agrobacterium* EHA 105 (pGlGLP130Hm) cultured in YEB agar medium (beef extract 5 g/L, yeast extract 1 g/L, peptone 5 g/L, sucrose 5 g/L, 2 mM MgSO₄, 15 g/L Bacto Agar) was transplanted into YEB liquid medium, and cultured at 25° C. at 180 rpm overnight, then centrifuged at 3000 rpm for 20 min, and harvested bacteria. The resultant bacteria was suspended in N6 liquid medium (N6 inorganic salts and vitamins, 30 g/L sucrose, 2 mg/L 2,4-D, pH=5.8) containing acetosyringone (10 mg/L) so that OD$_{630}$=0.15, and made it an *Agrobacterium* suspension for infection.

Germinated seeds prepared in III were placed in a 50 ml-tube, and the above *Agrobacterium* suspension for infection was added to the tube to immerse the seeds into it. After 1.5 min of immersion, *Agrobacterium* suspension was discarded, the germinated seeds were placed on a sterilized paper filter to remove extra water, placed into N6C12 medium (N6 inorganic salts and vitamins, 30 g/L sucrose, 2.8 g/L proline, 0.3 g/L casamino acid, 1 mg/L 2,4-D, b4g/L GelLight, pH=5.2), sealed with surgical tape, and cocultured at 28° C. in dark for 3 days. Then, the resultant was transplanted into N6C12TCH25 medium (N6 inorganic salts and vitamins, 30 g/L sucrose, 2.8 g/L proline, 0.3g/L casamino acid, 2 mg/L 2,4-D, 500 mg/L carbenicillin, 25 mg/L hygromycin, 4 g/L GelLight) and cultured for 1 week. Then, the germinated bud was cut from the scutellum tissue of the germinated seed.

Next, the scutellum tissue was cultured in N6C14TCH25 medium (N6 inorganic salts and vitamins, 30 g/L sucrose, 2.8 g/L proline, 0.3 g/L casamino acid, 4 mg/L 2,4-D, 500 mg/L carbenicillin, 25 mg/L hygromycin, 4g/L GelLight) for 1 week, and further cultured in MSRC medium (MS inorganic salts and vitamins, 30 g/L sucrose, 30 g/L sorbitole, 2 g/L casamino acid, 500 mg/L carbenicillin, 4 g/L GelLight). The bud or the seedling plant was redifferentiated during the $1^{st}$ to $2^{nd}$ month after coculture with EHA 105 (pGlbGLP130Hm). The redifferentiated bud or seedling plant were transplanted to rooting medium and grown, and a plantlet of about 20 cm high was obtained. Chromosomal DNA was extracted from the seedling plants with the use of DNeasy 96 Plant Kit (QIAGEN), and the existence of the gene encoding [$Ser^8$, $Gln^{26}$, $Asp^{34}$]-GLP-1 (7-36) was confirmed by PCR method.

At that time, as PCR primer to detect the gene encoding [$Ser^8$, $Gln^{26}$, $Asp^{34}$]-GLP-1 (7-36) introduced into the variable region of globulin gene, primers 3-1:5'-GGATCCATG-GCTAGCAAGGTCGTC-3' (SEQ ID NO:3) and 3-3:5'-GAT-CACTATCTCGTTGCATGCAACAC-3' (SEQ ID NO:4) were used. The obtained PCR reactant (about 700 bp) was analyzed by agarose gel electrophoresis and the existence of the gene encoding [$Ser^8$, $Gln^{26}$, $Asp^{34}$]-GLP-1 (7-36) in the chromosomal DNA was confirmed.

As a result, it was revealed that the above gene encoding [$Ser^8$, $Gln^{26}$, $Asp^{34}$]-GLP-1 (7-36) was introduced into about 3% of seed of Oryza sativa provided for Agrobacterium infection treatment.

The transformants of the plantlets of Oryza sativa confirmed to be introduced with the gene encoding [$Ser^8$, $Gln^{26}$, $Asp^{34}$]-GLP-1 (7-36) thus obtained, were transferred to soil and grown to harvest ripe seeds in room where sunlight enters.

V. Protein Analysis 10 mg of ripe seeds obtained in IV. was treated with 62.5 mM Tris-HCl (pH 6.8) extract buffer 250 µl containing 10% (v/v) glycerol, 0.25% (w/v) SDS, 5% 2-mercapto ethanol, at 100° C. for 5 min to extract all proteins of these seeds. The extract solution was provided for SDS-PAGE. For SDS-PAGE, 15% (w/v) polyacrylamide (acrylamide:N,N'-methyl-enebisacrylamide=30:0.8) gel was used.

The obtained gel image was analyzed with an analysis software, Image Gauge (Fujifilm), and the accumulation level of fusion protein wherein the gene encoding [$Ser^8$, $Gln^{26}$, $Asp^{34}$]-GLP-1 (7-36) was inserted into the variable region of globulin was examined. The results are shown in FIG. 5.

Comparative Example 1

Figure 5:
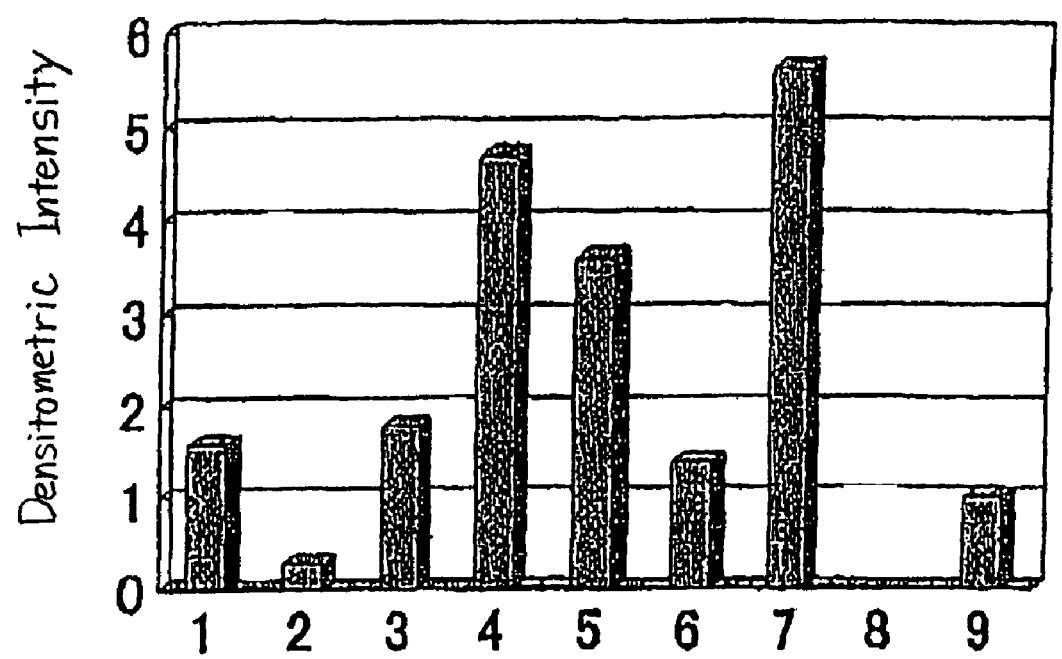
FIG. 5 shows accumulation level of the GLP-1 derivative fusion-protein in ripe seeds of *Oryza sativa* obtained in Example 1 and Comparative Example 1 in the Examples of the present invention.
Figure 6:
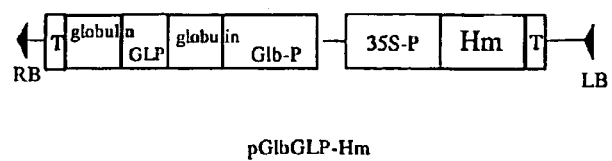
FIG. 6 shows a restriction map of the conventional vector pGlbGLP-Hm in the Examples of the present invention.

Except performing gene introduction to ripe seed of Oryza sativa by using the conventional vector pGlbGLP-Hm shown in FIG. 6 comprising rice globulin promoter, a globulin gene wherein the gene encoding [$Ser^8$, $Gln^{26}$, $Asp^{34}$]-GLP-1 (7-36) shown in SEQ ID NO: 1 was inserted into the variable region, and a gene fragment linked to polyadenilation signal of nopaline synthase, the gene introduction was performed in the same manner as Example 1 to redifferentiate the bud or the seedling plant. By regenerating a plant from the bud or the seedling plant, a transformed Oryza sativa was obtained and ripe seeds were collected. The ripe seeds were submitted to protein analysis. The results are shown in FIG. 5.

As it is clear from FIG. 5, the fusion protein wherein the gene encoding [$Ser^8$, $Gln^{26}$, $Asp^{34}$]-GLP-1 (7-36) is inserted into the variable region of globulin was highly accumulated in the rice ripe seeds produced in Example 1, and showed about 6-fold level at maximum, compared with Comparative Example 1 (FIG. 5).

Example 2

I. Synthesis of GLP-1 Derivative

The GLP-1 derivatives shown in the following were synthesized by solid phase synthesis using Model 430A peptide synthesizer (PE-Applied Biosystems, Foster City, Calif.), purified by HPLC. The synthesized materials were confirmed by mass spectrum. Derivatives with 95% or more purity were used for in vitro and in vivo examination.

Comparative Production Example 1

GLP-1 (7-36 amide) (Native GLP-1)

Comparative Production Example 2

[$Ser^8$]-GLP-1 (7-36 amide)

Comparative Production Example 3

[$Gly^8$]-GLP-1 (7-36 amide)

Production Example 1

[$Gln^{26}$, $Asn^{34}$]-GLP-1 (7-36 amide)

(The amino acid sequence of non-amide body of Production Example 1 is shown in SEQ ID NO:5).

Production Example 2

[$Ser^8$, $Gln^{26}$, $Asp^{34}$]-GLP-1 (7-36)

Production Example 3

[$Ser^8$, $Gln^{26}$, $Asn^{34}$]-GLP-1 (7-36)

(The amino acid sequence of Production Example 3 is shown in SEQ ID NO:6).

II. Cyclic AMP Production Activity of the GLP-1 Derivative

Expression vectors were constructed according to the published DNA sequence (Graziano et al, Biochem Biophys Res Com, 196:141-146, 1993) of the human GlP-1 receptor. Chinese hamster ovary CHO-K1 cells were transformed with the vectors, and the recombinant CHO-K1 cells which express human GLP-1 receptors were obtained. The human GLP-1 receptor-expression cells were planted in 24-well plates at $1 \times 10^4$ cells/ml/well, and were used for assay 3 days later.

Figure 7:
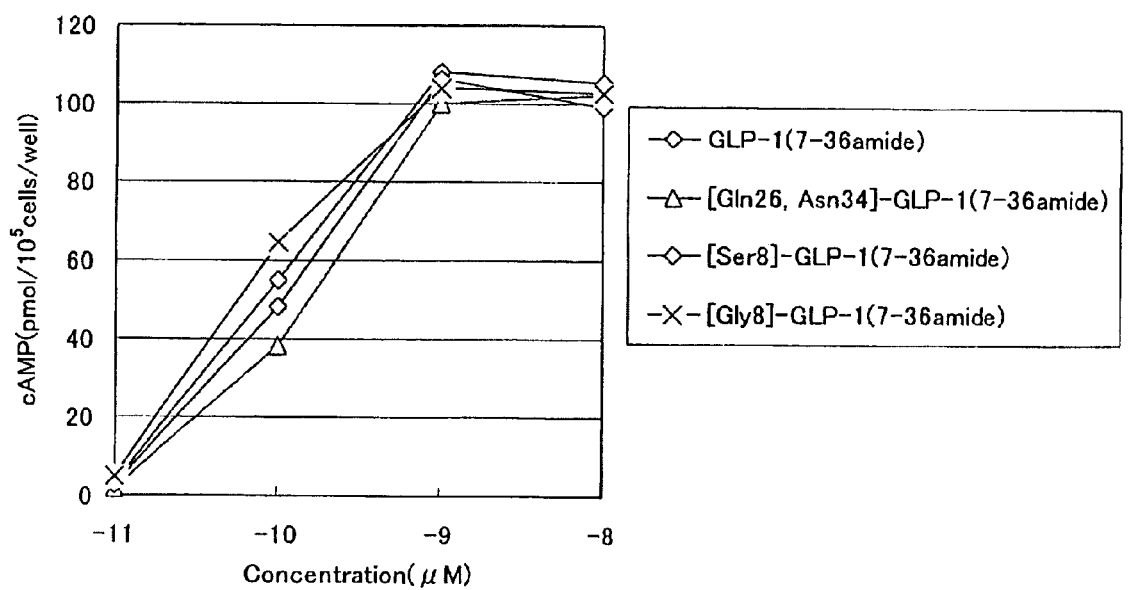
FIG. 7 shows the measured result of cyclic AMP production activity of GLP-1 (7-36 amide) (native GLP-1) in the Comparative Production Example 1, [$Ser^8$]-GLP-1 (7-36 amide) in the Comparative Production Example 2, [$Gly^8$]-GLP-1 (7-36 amide) in the Comparative Production Example 3, and [$Gln^{26}$, $Asn^{34}$]-GLP-1 (7-36 amide) in the Production Example 1 according to the method shown in Example 2 in the Examples of the present invention.

The assay was performed as follows: the cells were incubated in the presence of the GLP-1 derivatives in a buffer (PBS, 5.6 mM glucose, 1 mM isobutyl methyl xanthine, 20 µM Ro20-1724, 0.5% BSA, pH 7.4) at 37° C. for 30 min. 10 µl of 5N hydrochloric acid was added to the buffer to stop the incubation. Cyclic AMP formed in the cells by the reaction of various GLP-1 derivatives and GLP-1 receptors was measured by enzyme immunoassay with cAMP-Screen™ system (Appplied Biosystems). FIG. 7 shows cyclic AMP production activity of various GLP-1 derivatives.

As a result, [$Ser^8$]-GLP-1 (7-36amide), [$Gly^8$]-GLP-1 (7-36 amide) and [$Gln^{26}$, $Asn^{34}$]-GLP-1 (7-36 admide) had the same level of cyclic AMP production activity as native GLP-1.

Example 3

Trypsin resistance of [Gln$^{26}$, Asn$^{34}$]-GLP-1 (7-36 amide) of Production Example 1 was examined by measuring cyclic AMP production activity in the same manner as Example 2, after trypsin treatment.

In other words, the above GLP-1 derivative obtained by synthesis were dissolved in 50 mM ammonium hydrogen carbonate solution (pH 7.8), so that the concentration becomes 500 μg/mg. 5 μl of 500 μg/ml trypsin solution (Promega: Cat. No. V5113) was added to 100 μl of this solution, and reacted at 37° C. for 1 hour. The reaction was stopped by adding 1200 μl of 71.5% ethanol (final 65%). The supernatant was collected by centrifugation at 15,000 rpm at 4° C. for 5 min, and evaporation was carried out. The dried solids were dissolved in distilled water and used for measuring activity.

FIG. 8 shows the concentration dependency of [Gln$^{26}$, Asn$^{34}$]-GLP-1 (7-36 amide) activity before and after trypsin treatment. [Gln$^{26}$, Asn$^{34}$]-GLP-1 (7-36 amide) showed no difference of activity before and after trypsin treatment, and it was revealed that it was resistant to trypsin.

Example 4

Stability to pepsin of the GLP-1 derivative in ripe seeds of *Oryza sativa* was examined.

Polished rice and powder thereof of the ripe seeds of *Oryza sativa* obtained in Example 1 were used and cooked with 1.9-fold amount of water at 100° C. by heating for 15 min. Those in form of granules were crushed and homogenized, diluted 5-fold with distilled water to make a sample. Those in powder were directly diluted 5-fold with distilled water to make a sample. On the other hand, as for synthetic GLP-1 (7-36 amide), [Ser$^8$, Gln$^{26}$, Asp$^{34}$]-GLP-1 (7-36) and [Ser$^8$, Gln$^{26}$, Asn$^{34}$]-GLP-1 (7-36), a 10 μg/ml solution was prepared with 0.2% BSA solution as a sample.

A 1/10-amount of artificial gastric juice (pH 1.2) of 10-fold concentration containing 7.6 mg/ml pepsin was added to each sample, and the liquid was neutralized with NaOH after reaction at 37° C. for 1 hour. Then, as for GLP-1 (7-36amide), [Ser$^8$, Gln$^{26}$, Asp$^{34}$]-GLP-1 (7-36) and [Ser$^8$, Gln$^{26}$, Asn$^{34}$]-GLP-1 (7-36), after extracting the protein and getting GLP-1 simple substance by trypsin treatment as for those derived from rice, the activity according to cyclic AMP production was measured. As a result, it was revealed that the activity of synthetic GLP-1 derivative was completely lost by pepsin treatment, while 31-65% of GLP-1 activity remained in rice (FIG. 9).

From these results, it can be estimated that GLP-1 derivatives contained in rice ripe seeds are not easily digested by pepsin and can reach the small intestine by passing through the stomach.

Example 5

Fusion protein with [Ser$^8$, Gln$^{26}$, Asp$^{34}$]-GLP-1 (7-36) and globulin was extracted from ripe seeds of *Oryza sativa* obtained in Example 1 with 0.025 M sodium hydroxide solution, and the extract was diluted 15-fold with 50 mM ammonium hydrogen carbonate pH 7.8. To this diluent, 6 μl of 83 μg/ml trypsin solution (Promega: Cat. No. V5113) was added. The resultant was reacted at 37° C. for 1, 2, 4, 6 or 20 hours, and then the reaction was stopped by adding 1200 μl of 71.5% ethanol (final 65%). The supernatant was collected by centrifugation at 15,000 rpm at 4° C. for 5 min and evaporation was carried out. The dried solids were dissolved in distilled water and the activity was measured.

Figure 10:
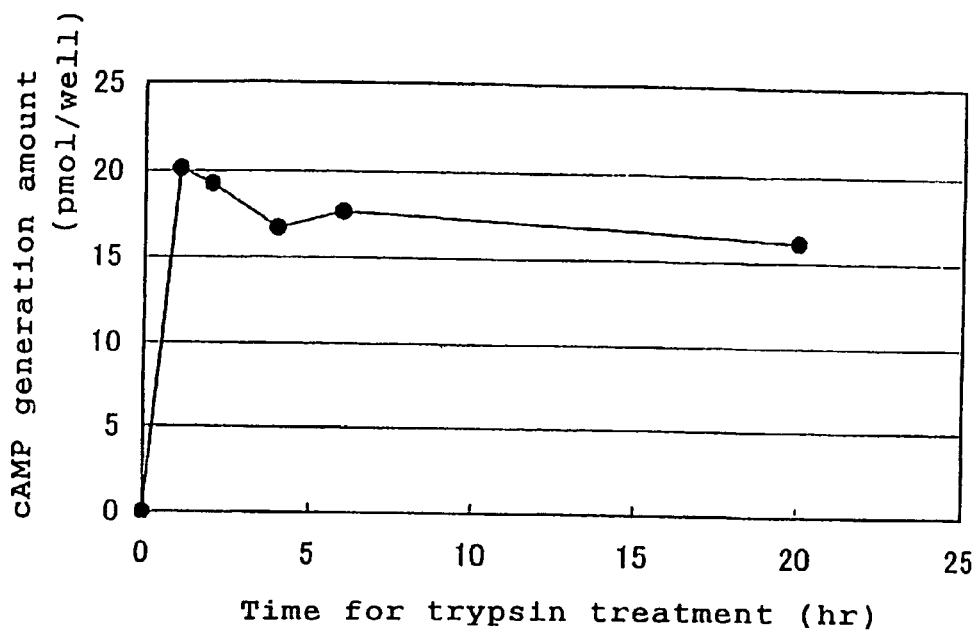
FIG. 10 shows the relationship between trypsin treatment time and cyclic AMP production activity of the extracted fraction after extracting [Ser$^8$, Gln$^{26}$, Asp$^{34}$]-GLP-1 (7-36) as fusion protein from ripe seeds of Oryza sativa according to the method shown in Example 5 in the Examples of the present invention.

FIG. 10 shows the relationship between trypsin treatment time and activity of [Ser$^8$, Gln$^{26}$, Asp$^{34}$]-GLP-1 (7-36) which has been expressed in ripe seeds of *Oryza sativa* and obtained as fusion protein. Cyclic AMP production activity appears only by trypsin treatment, and the activity was maintained regardless of the trypsin treatment time. From these results, it was revealed that [Ser$^8$, Gln$^{26}$, Asp$^{34}$]-GLP-1 (7-36) is expressed in ripe seeds of *Oryza sativa* as a form having the activity and trypsin-resistance. Therefore, it is estimated that [Ser$^8$, Gln$^{26}$, Asp$^{34}$]-GLP-1 (7-36) contained in ripe seeds if *Oryza sativa* by the GLP-1 derivative expression can be absorbed without being degraded by trypsin in the small intestine.

Example 6

Trypsin-resistance of [Ser$^8$, Gln$^{26}$, Asn$^{34}$]-GLP-1 (7-36) and [Ser$^8$, Gln$^{26}$, Asp$^{34}$]-GLP-1 (7-36) was examined by measuring cyclic AMP production activity in the same manner as Example 2 after trypsin treatment.

In other words, 8 μl of the above synthetic GLP-1 derivative, diluted to 10 μg/ml with 0.2% bovine serum albumin solution was added to 112 μl of 50 mM ammonium hydrogen carbonate (pH 7.8) and 6 μl of 83 μg/ml trypsin solution (Promega:Cat. No.V5113) for reaction at 37° C. for 1 hour. The reaction was stopped by adding 1200 μl of 71.5% ethanol (final 65%). The supernatant was collected by centrifugation of 15,000 rpm at 4° C. for 5 min and evaporation was carried out. The dried solids were dissolved in distilled water and used for measuring the activity.

Figure 11:
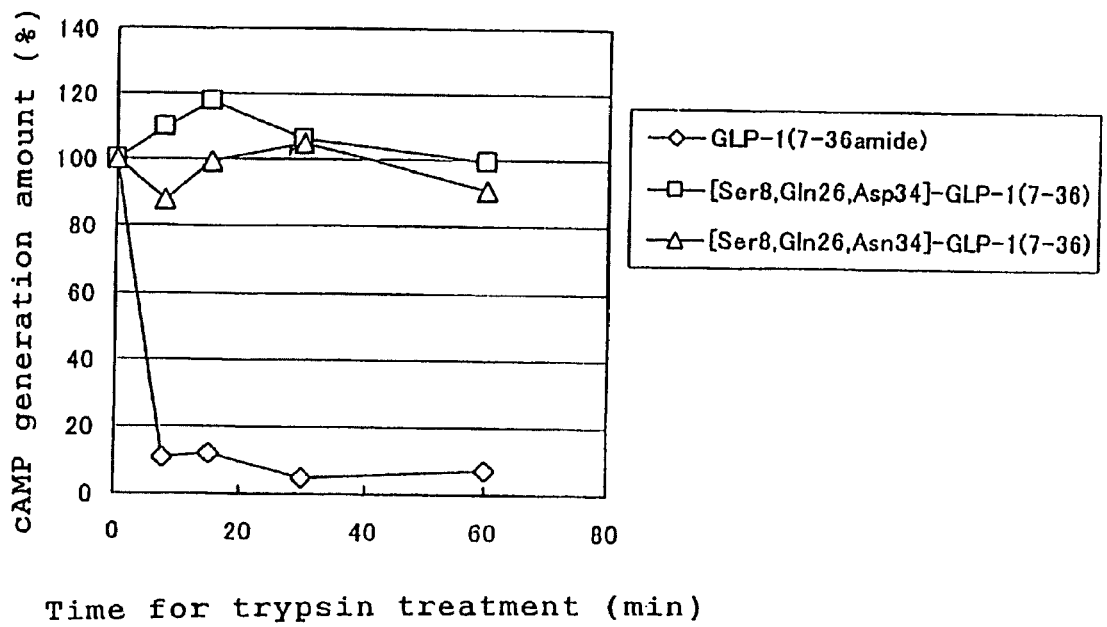
FIG. 11 shows the comparison of the trypsin resistance using GLP-1 (7-36 amide) (native GLP-1) in the Comparative Production Example 1, [Ser$^8$, Gln$^{26}$, Asp$^{34}$]-GLP-1 (7-36) in the Production Example 2, and [Ser$^8$, Gln$^{26}$, Asn$^{34}$]-GLP-1 (7-36) in the Production Example 3 according to the method shown in Example 6 in the Examples of the present invention.

FIG. 11 shows the variation in activity against trypsin treatment time of GLP-1 (7-36 amide), [Ser$^8$, Gln$^{26}$, Asn$^{34}$]-GLP-1 (7-36) and [Ser$^8$, Gln$^{26}$, Asp$^{34}$]-GLP-1 (7-36). Compared with native GLP-1 (7-36 amide), [Ser$^8$, Gln$^{26}$, Asn$^{34}$]-GLP-1 (7-36) and [Ser$^8$, Gln$^{26}$, Asp$^{34}$]-GLP-1 (7-36) showed no variation in activity by trypsin treatment, and they were revealed to be trypsin resistant.

Example 7

It was examined whether the GLP-1 derivative of the present invention shows significant DDP-IV resistance compared with native GLP-1. 5000 pM of GLP-1 (7-36 amide) (native GLP-1), 500 pM of [Ser$^8$, Gln$^{26}$, Asn$^{34}$]-GLP-1 (7-36), and 5000 pM of [Ser$^8$, Gln$^{26}$, Asp$^{34}$]-GLP-1 (7-36) were mixed separately with 40 μU/μl of DPP-IV (Sigma, D7052) for reaction at 37° C. for 0, 15, 30 and 60 min, the mixtures were extracted with 2-fold amount of ethanol and the extracts were dried with centrifugal evaporator. The obtained dried solids were dissolved in distilled water containing 1% BSA and were reacted with GLP-1 receptor-expression cells to measure the cyclic AMP production level. FIG. 12 shows the comparison of cyclic AMP production activity with 100% for those without DPP-IV treatment. Compared to GLP-1 (7-36 amide), [Ser$^8$, Gln$^{26}$, Asn$^{34}$]-GLP-1 (7-36) and [Ser$^8$, Gln 26, Asp$^{34}$]-GLP-1 (7-36) showed obvious DPP-IV resistance.

Example 8

Insulin-secretion-promoting activity of GLP-1 derivative of the present invention was examined. Langerhans islets were extracted from ICR mouse pancreas with collagenase, 2 to 3 Langerhans islets were placed per well of 24-well plates, and cultured overnight. Then, the GLP-1 derivative of the present invention dissolved in Krebs-Ringer buffer containing 16.7 mM glucose, 0.2% BSA and 10 mM hepes was added, incubated at 37° C. for 30 min and insulin concentration in the supernatant was measured with an enzyme immunoassay kit (Shibayagi).

Amount-dependent insulin secretion-promoting activity was observed in any of the peptides of GLP-1 (7-36 amide), [$Ser^8$, $Gln^{26}$, $Asp^{34}$]-GLP-1 (7-36) and [$Ser^8$, $Gln^6$, $Asn^{34}$]-GLP-1 (7-36). Particularly, a strong insulin secretion-promoting activity was observed in [$Ser^8$, $Gln^{26}$, $Asn^{34}$]-GLP-1 (7-36) at high concentration (FIG. 13).

Example 9

Hypoglycemic effect in oral glucose tolerance test (OGTT) by the GLP-1 derivative subcutaneous administration was examined.

Figure 14:
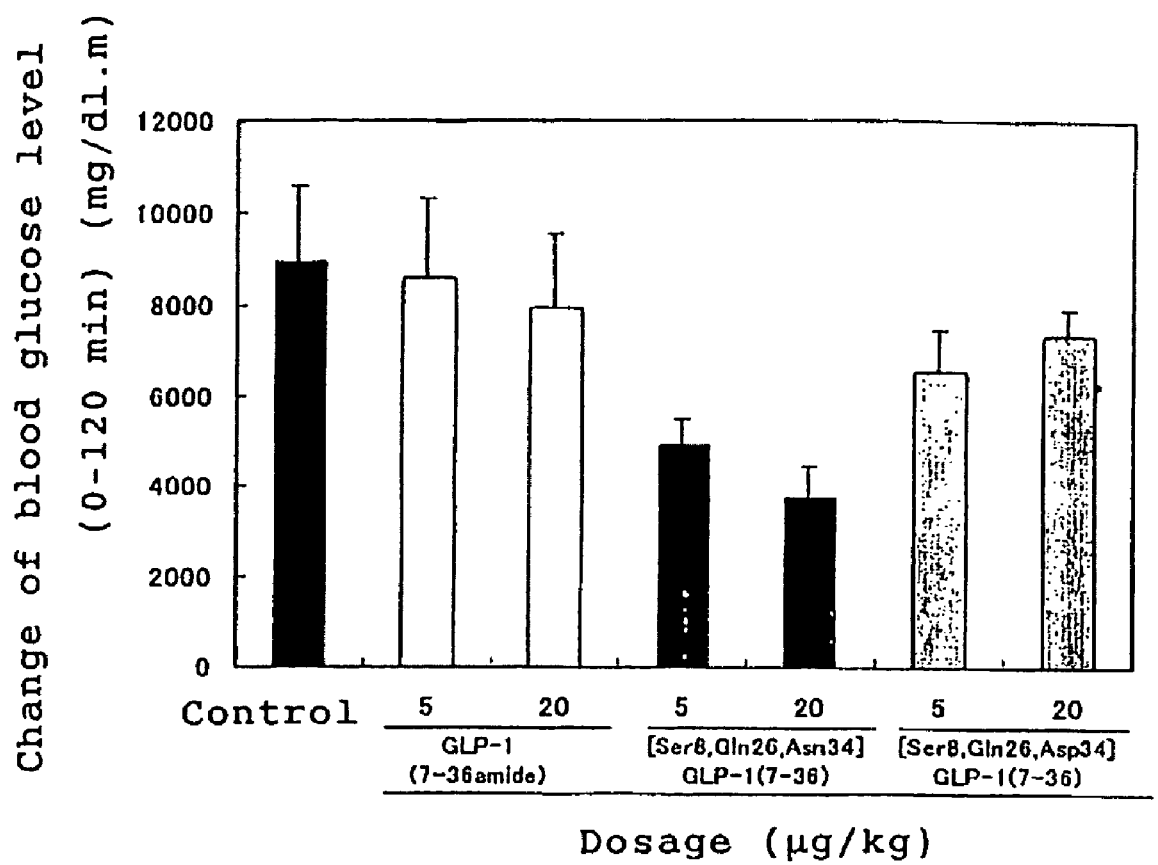
FIG. 14 shows the comparison of the hypoglycemic effect in oral glucose tolerance test with mice using GLP-1 (7-36 amide) (native GLP-1) in the Comparative Production Example 1, [Ser$^8$, Gln$^{26}$, Asp$^{34}$]-GLP-1 (7-36) in the Production Example 2, and [Ser$^8$, Gln$^{26}$, Asn$^{34}$]-GLP-1 (7-36) in the Production Example 3 according to the method shown in Example 9 in the Examples of the present invention, and shows an area under the curve of the graph indicating variation of blood glucose level from 0 to 120 min in FIG. 15 as blood glucose level variation.
Figure 15:
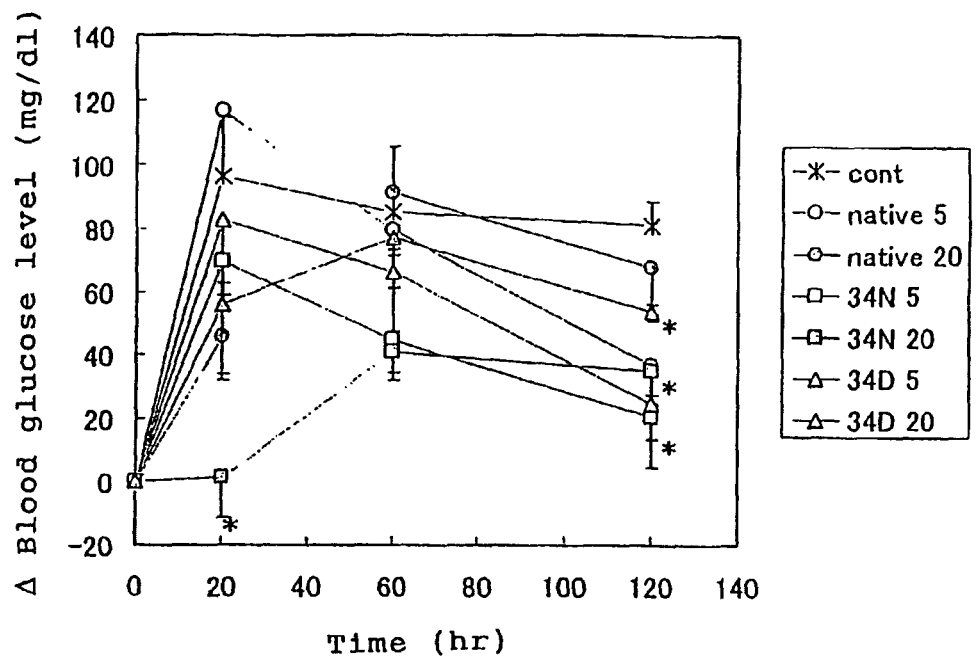
FIG. 15 shows comparison of the hypoglycemic effect in oral glucose tolerance test with mice using GLP-1 (7-36 amide) (native GLP-1) in the Comparative Production Example 1, [Ser$^8$, Gln$^{26}$, Asp$^{34}$]-GLP-1 (7-36) in the Production Example 2, and [Ser$^8$, Gln$^{26}$, Asn$^{34}$]-GLP-1 (7-36) in the Production Example 3 according to the method shown in Example 9 in the Examples of the present invention, and shows the change of blood glucose level from 0 to 120 min.

1 g/kg glucose was orally administered to mice fasted overnight, and immediately, GLP-1 (7-36 amide), [$Ser^8$, $Gln^{26}$, $Asn^{34}$]-GLP-1 (7-36) or [$Ser^8$, $Gln^{26}$, $Asp^{34}$]-GLP-1 (7-36) was administered dorsal subcutaneously (5, 20 μg/kg). Physiological saline was administered to the control group. Before loading glucose and 20, 60, 120 min after loading, blood was collected chronologically from subocular venous plexus, to measure blood glucose level. In the GLP-1 derivative, it was observed that the peak value of blood glucose increase has a tendency to decrease, and a strong action was confirmed in [$Ser^8$, $Gln^{26}$, $Asn^{34}$]-GLP-1 (7-36) (FIG. 14). Moreover, the action continued until 120 min after the administration (FIG. 15). It was revealed that by the modification of the GLP-1 peptide, the stability in blood in vivo significantly increased and the sustainability was assured.

INDUSTRIAL APPLICABILITY

The present invention provides a substance production system by the method for producing a plant storage organ in which a recombinant protein is highly produced as a safe and an efficient substance production system at low cost with the use of genetic engineering. The method of the present invention can provide food in which ingredient useful for promoting health is significantly accumulated. Further, the method of the present invention can be a basic technology to generate high-value added plant which produces valuable substance as pharmaceuticals or industrial material.

Further, the present invention encompasses the production of a GLP-1 which is known as a hormone secreted from the digestive tract by food intake and acting on the pancreas to stimulate glucose-dependent insulin secretion, according to the method of the present invention.

In addition, the novel GLP-1 derivative provided in the present invention has excellent properties: it is resistant to a digestive enzyme such as trypsin which causes problem on taking it when the GLP-1 is used, and it further has resistance to dipeptidylpeptidase IV which causes problem on stability in the blood plasma after it is taken and absorbed, therefore it can be expected for the use as pharmaceuticals. That is, it is possible for the GLP-1 derivative of the present invention to express its therapeutic effect even when it is orally taken, and for instance, even when it is expressed in a plant storage organ by the method of the present invention and orally taken, it can be absorbed from the small intestine without being degraded and express its therapeutic effect. Accordingly, as the GLP-1 derivative provided by the present invention enhances the possibility of the clinical application of the GLP-1, and it is believed that it helps improve quality of life of diabetic patients and obese patients.

The invention claimed is:

1. A GLP-1 derivative consisting of an amino acid sequence of a GLP-1 peptide selected from the group consisting of GLP-1(7-36), GLP-1(7-37), GLP-1(7-36 amide), and GLP-1(7-37 amide), wherein glutamine is substituted at the 26$^{th}$ position and asparagine is substituted at the 34$^{th}$ position in the amino acid sequence, wherein the GLP-1 derivative has resistance to trypsin.

2. The GLP-1 derivative according to claim 1, wherein serine or glycine is substituted at the 8$^{th}$ position in the amino acid sequence, wherein the GLP-1 derivative has resistance to trypsin and dipeptidylpeptidase IV.

3. The GLP-1 derivative according to claim 2, wherein the GLP-1 derivative consists of the amino acid sequence shown in SEQ ID NO: 6.

4. The GLP-1 derivative according to claim 1, wherein the GLP-1 derivative consists of the amino acid sequence shown in SEQ ID NO: 5.

* * * * *